US008277459B2

(12) United States Patent
Sand et al.

(10) Patent No.: US 8,277,459 B2
(45) Date of Patent: Oct. 2, 2012

(54) METHODS AND DEVICES FOR TREATING A STRUCTURAL BONE AND JOINT DEFORMITY

(75) Inventors: Paul M. Sand, Redwood City, CA (US); Peter T. Keith, Lanesboro, MN (US); John Avi Roop, Palo Alto, CA (US); Joshua Baltzell, Palo Alto, CA (US); Jason W. Lettmann, Menlo Park, CA (US)

(73) Assignee: Tarsus Medical Inc., Menlo Park, CA (US)

( * ) Notice: Subject to any disclaimer, the term of this patent is extended or adjusted under 35 U.S.C. 154(b) by 455 days.

(21) Appl. No.: 12/567,314

(22) Filed: Sep. 25, 2009

(65) Prior Publication Data

US 2011/0077656 A1 Mar. 31, 2011

(51) Int. Cl.
*A61B 17/58* (2006.01)
*A61B 17/56* (2006.01)

(52) U.S. Cl. ........................................ 606/96; 606/86 R
(58) Field of Classification Search .............. 606/82–85, 606/86 R–89, 96–99
See application file for complete search history.

(56) References Cited

U.S. PATENT DOCUMENTS

| | | | |
|---|---|---|---|
| 2,291,413 A | 7/1942 | Siebrandt | |
| 3,867,929 A | 2/1975 | Joyner et al. | |
| 3,880,155 A | 4/1975 | Rosoff | |
| 3,987,559 A | 10/1976 | Roberts | |
| 4,069,824 A | 1/1978 | Weinstock | |
| 4,213,208 A | 7/1980 | Marne | |
| 4,240,214 A | 12/1980 | Sigle et al. | |
| 4,244,359 A | 1/1981 | Dieterich | |
| 4,255,875 A | 3/1981 | Gilkerson | |
| 4,263,902 A | 4/1981 | Dieterich | |
| 4,266,553 A | 5/1981 | Faiella | |
| 4,300,294 A | 11/1981 | Riecken | |
| 4,314,412 A | 2/1982 | Anderson et al. | |
| 4,317,293 A | 3/1982 | Sigle et al. | |
| 4,393,876 A | 7/1983 | Dieterich | |
| 4,409,974 A | 10/1983 | Freedland | |
| 4,414,964 A | 11/1983 | Farino et al. | |
| 4,439,934 A | 4/1984 | Brown | |
| 4,510,699 A | 4/1985 | Nakamura et al. | |
| 4,583,303 A | 4/1986 | Laiacona et al. | |
| 4,597,195 A | 7/1986 | Dananberg | |
| 4,603,698 A | 8/1986 | Guttmann Cherniak | |
| 4,604,997 A | 8/1986 | De Bastiani et al. | |
| 4,608,988 A | 9/1986 | Dananberg | |

(Continued)

FOREIGN PATENT DOCUMENTS
EP 40782 A2 12/1981

(Continued)

OTHER PUBLICATIONS

Invitation to Pay Additional Fees issued in PCT/US2011/039041, mailed Sep. 6, 2011, 4 pages.

(Continued)

*Primary Examiner* — Kevin T Truong
*Assistant Examiner* — Christopher Beccia
(74) *Attorney, Agent, or Firm* — Faegre Baker Daniels LLP

(57) ABSTRACT

The various embodiments disclosed herein relate to implantable devices for the treatment of a structural bone and deformity. More specifically, the various embodiments include systems, devices, and methods for implantation of a flexible or tension band for treating such a deformity, including hallux valgus.

7 Claims, 10 Drawing Sheets

U.S. PATENT DOCUMENTS

| | | |
|---|---|---|
| 4,632,103 A | 12/1986 | Fabricant et al. |
| 4,644,940 A | 2/1987 | Nakamura |
| 4,676,801 A | 6/1987 | Lundeen |
| 4,726,127 A | 2/1988 | Barouk |
| 4,729,369 A | 3/1988 | Cook |
| 4,738,255 A | 4/1988 | Goble et al. |
| RE32,698 E | 6/1988 | Brown |
| 4,813,162 A | 3/1989 | Harris |
| 4,819,644 A | 4/1989 | Cherniak |
| 4,841,647 A | 6/1989 | Turucz |
| 4,842,931 A | 6/1989 | Zook |
| 4,852,556 A | 8/1989 | Groiso |
| 4,856,505 A | 8/1989 | Shaffer et al. |
| 4,876,758 A | 10/1989 | Rolloff et al. |
| 4,901,453 A | 2/1990 | Gaynor |
| 4,930,504 A | 6/1990 | Diamantopoulos et al. |
| 4,940,046 A | 7/1990 | Jacoby |
| 4,969,277 A | 11/1990 | Williams |
| 4,976,712 A * | 12/1990 | VanderSlik ............ 606/59 |
| 5,005,575 A | 4/1991 | Geri |
| 5,012,596 A | 5/1991 | Schiller |
| 5,035,069 A | 7/1991 | Minden |
| 5,092,347 A | 3/1992 | Shaffer et al. |
| 5,094,226 A | 3/1992 | Medcalf et al. |
| 5,098,421 A | 3/1992 | Zook |
| 5,138,777 A | 8/1992 | Darby |
| 5,167,665 A | 12/1992 | McKinney |
| 5,174,052 A | 12/1992 | Schoenhaus et al. |
| 5,250,049 A | 10/1993 | Michael |
| D341,424 S | 11/1993 | Lurie |
| 5,272,139 A | 12/1993 | Cary, Jr. |
| 5,306,301 A | 4/1994 | Graf et al. |
| 5,350,383 A | 9/1994 | Schmieding et al. |
| RE34,753 E | 10/1994 | Groiso |
| 5,497,789 A | 3/1996 | Zook |
| 5,529,075 A | 6/1996 | Clark |
| 5,537,764 A | 7/1996 | Prahl |
| 5,539,020 A | 7/1996 | Bracken et al. |
| 5,571,139 A * | 11/1996 | Jenkins, Jr. ............ 606/232 |
| 5,601,565 A | 2/1997 | Huebner |
| 5,607,756 A | 3/1997 | Yamauchi et al. |
| 5,611,801 A * | 3/1997 | Songer ............ 606/308 |
| 5,617,651 A | 4/1997 | Prahl |
| 5,640,779 A | 6/1997 | Rolloff et al. |
| 5,645,588 A | 7/1997 | Graf et al. |
| 5,665,060 A | 9/1997 | Fabricant |
| 5,665,112 A | 9/1997 | Thal |
| 5,685,834 A | 11/1997 | Barth |
| H1706 H | 1/1998 | Mason |
| 5,713,903 A | 2/1998 | Sander et al. |
| 5,725,585 A | 3/1998 | Zobel |
| 5,728,136 A * | 3/1998 | Thal ............ 606/232 |
| 5,788,697 A * | 8/1998 | Kilpela et al. ............ 606/74 |
| 5,792,093 A | 8/1998 | Tanaka |
| 5,797,913 A * | 8/1998 | Dambreville et al. ........ 606/916 |
| 5,802,737 A | 9/1998 | Beppu |
| 5,810,822 A | 9/1998 | Mortier |
| 5,843,085 A | 12/1998 | Graser |
| 5,853,293 A | 12/1998 | Weber et al. |
| 5,919,194 A | 7/1999 | Anderson |
| 5,921,986 A * | 7/1999 | Bonutti ............ 606/60 |
| 5,962,011 A | 10/1999 | DeVillez et al. |
| 6,001,101 A | 12/1999 | Augagneur et al. |
| 6,068,648 A * | 5/2000 | Cole et al. ............ 606/232 |
| 6,091,000 A | 7/2000 | Haynes |
| 6,093,163 A | 7/2000 | Chong et al. |
| 6,203,545 B1 | 3/2001 | Stoffella |
| 6,238,357 B1 | 5/2001 | Kawaguchi et al. |
| D443,694 S | 6/2001 | Ford |
| 6,248,109 B1 | 6/2001 | Stoffella |
| 6,248,788 B1 | 6/2001 | Robbins et al. |
| 6,264,677 B1 | 7/2001 | Simon et al. |
| 6,283,973 B1 | 9/2001 | Hubbard et al. |
| 6,315,749 B1 | 11/2001 | Sunayama |
| 6,318,373 B1 | 11/2001 | Kasahara |
| 6,319,270 B1 | 11/2001 | Grafton et al. |
| 6,348,053 B1 | 2/2002 | Cachia |
| 6,367,087 B1 | 4/2002 | Spillman et al. |
| 6,391,031 B1 | 5/2002 | Toomey |
| 6,406,234 B2 | 6/2002 | Frigg |
| 6,424,864 B1 | 7/2002 | Matsuura |
| 6,447,783 B1 | 9/2002 | Yayon |
| 6,478,761 B2 | 11/2002 | Bracamonte-Sommer |
| 6,481,120 B2 | 11/2002 | Xia et al. |
| 6,514,222 B2 | 2/2003 | Cook |
| 6,547,792 B1 | 4/2003 | Tsuji et al. |
| 6,547,800 B2 | 4/2003 | Foerster et al. |
| 6,569,188 B2 | 5/2003 | Grafton et al. |
| 6,583,114 B2 | 6/2003 | Vickery |
| 6,604,301 B1 | 8/2003 | Manoli, II et al. |
| 6,616,665 B2 | 9/2003 | Grafton et al. |
| 6,629,943 B1 | 10/2003 | Schroder |
| 6,643,956 B2 | 11/2003 | Mawusi et al. |
| 6,684,532 B2 | 2/2004 | Greene et al. |
| 6,689,136 B2 | 2/2004 | Stoffella |
| 6,716,234 B2 | 4/2004 | Grafton et al. |
| 6,800,063 B2 | 10/2004 | Iwata |
| 6,862,481 B1 | 3/2005 | Demian |
| 6,874,258 B2 | 4/2005 | Clough et al. |
| 6,887,243 B2 | 5/2005 | Culbert |
| 6,887,259 B2 | 5/2005 | Lizardi |
| 6,889,088 B2 | 5/2005 | Demian |
| 6,890,333 B2 | 5/2005 | von Hoffmann et al. |
| 6,902,799 B2 | 6/2005 | Chikamori |
| 6,908,465 B2 | 6/2005 | von Hoffmann et al. |
| 6,909,513 B1 | 6/2005 | Fujita et al. |
| 6,910,287 B2 | 6/2005 | Truelsen |
| 6,942,668 B2 | 9/2005 | Padget et al. |
| 6,964,645 B1 | 11/2005 | Smits |
| 6,991,636 B2 | 1/2006 | Rose |
| 7,008,428 B2 | 3/2006 | Cachia et al. |
| 7,013,583 B2 | 3/2006 | Greene et al. |
| 7,055,268 B2 | 6/2006 | Ha |
| 7,056,885 B1 | 6/2006 | Jeffers et al. |
| 7,062,866 B2 | 6/2006 | Bussler |
| 7,070,601 B2 | 7/2006 | Culbert et al. |
| 7,097,647 B2 | 8/2006 | Segler |
| 7,141,545 B2 | 11/2006 | Pike et al. |
| 7,175,667 B2 | 2/2007 | Saunders et al. |
| 7,192,411 B2 | 3/2007 | Gobet et al. |
| 7,217,853 B2 | 5/2007 | Kulichikhin et al. |
| 7,253,266 B2 | 8/2007 | Shimkets et al. |
| 7,263,788 B2 | 9/2007 | Johnson |
| 7,266,910 B2 | 9/2007 | Ingimundarson |
| 7,270,644 B2 | 9/2007 | Ingimundarson |
| 7,276,244 B2 | 10/2007 | Radovic |
| 7,287,293 B2 | 10/2007 | Cook et al. |
| 7,291,175 B1 | 11/2007 | Gordon |
| 7,291,483 B2 | 11/2007 | Shimkets et al. |
| 7,325,323 B2 | 2/2008 | Katsu et al. |
| 7,326,211 B2 | 2/2008 | Padget et al. |
| 7,383,089 B2 | 6/2008 | Demian |
| 7,392,605 B2 | 7/2008 | Hatfield et al. |
| 7,396,338 B2 | 7/2008 | Huber et al. |
| 7,485,135 B2 | 2/2009 | Steiger et al. |
| 7,493,810 B2 | 2/2009 | Walczyk et al. |
| 7,513,880 B2 | 4/2009 | Ingimundarson et al. |
| 7,572,258 B2 | 8/2009 | Stiernborg |
| 7,625,395 B2 | 12/2009 | Muckter |
| 7,875,058 B2 * | 1/2011 | Holmes, Jr. ............ 606/232 |
| 2001/0027583 A1 | 10/2001 | Rothbart |
| 2001/0034956 A1 | 11/2001 | Mawusi et al. |
| 2002/0007134 A1 | 1/2002 | Bracamonte-Sommer |
| 2002/0022862 A1 | 2/2002 | Grafton et al. |
| 2002/0032466 A1 | 3/2002 | Grafton et al. |
| 2002/0056209 A1 | 5/2002 | Clough et al. |
| 2002/0058036 A1 | 5/2002 | Jeffers et al. |
| 2002/0062140 A1 | 5/2002 | Demian |
| 2002/0077281 A1 | 6/2002 | Vickery |
| 2002/0138026 A1 | 9/2002 | Cook |
| 2002/0162250 A1 | 11/2002 | Campbell et al. |
| 2002/0193309 A1 | 12/2002 | Yayon |
| 2003/0005601 A1 | 1/2003 | Kasahara |
| 2003/0023268 A1 | 1/2003 | Lizardi |
| 2003/0040750 A1 | 2/2003 | Stoffella |
| 2003/0045881 A1 | 3/2003 | Barouk et al. |
| 2003/0093920 A1 | 5/2003 | Greene et al. |

| | | |
|---|---|---|
| 2003/0105193 A1 | 6/2003 | Wang |
| 2003/0134792 A1 | 7/2003 | Pike et al. |
| 2003/0148692 A1 | 8/2003 | Chikamori |
| 2003/0152637 A1 | 8/2003 | Chasin et al. |
| 2003/0172553 A1 | 9/2003 | Truelsen |
| 2003/0186433 A1 | 10/2003 | Shimkets et al. |
| 2003/0187372 A1 | 10/2003 | Iwata |
| 2003/0225356 A1 | 12/2003 | Kulichikhin et al. |
| 2004/0019308 A1 | 1/2004 | Chow |
| 2004/0031169 A1 | 2/2004 | Jensen et al. |
| 2004/0039319 A1 | 2/2004 | Calatayud Carral |
| 2004/0045194 A1 | 3/2004 | Kumai |
| 2004/0093746 A1 | 5/2004 | Varsallona |
| 2004/0103561 A1 | 6/2004 | Campbell et al. |
| 2004/0107604 A1 | 6/2004 | Ha |
| 2004/0123495 A1 | 7/2004 | Greene et al. |
| 2004/0127907 A1* | 7/2004 | Dakin et al. ............... 606/72 |
| 2004/0156931 A1 | 8/2004 | Burch et al. |
| 2004/0161481 A1 | 8/2004 | Burch et al. |
| 2004/0168329 A1 | 9/2004 | Ishimaru |
| 2004/0168353 A1 | 9/2004 | Bussler |
| 2004/0186182 A1 | 9/2004 | Burch et al. |
| 2004/0191338 A1 | 9/2004 | Burch et al. |
| 2004/0194348 A1 | 10/2004 | Campbell et al. |
| 2004/0194352 A1 | 10/2004 | Campbell et al. |
| 2004/0210234 A1 | 10/2004 | Coillard et al. |
| 2004/0243197 A1 | 12/2004 | Demian |
| 2005/0019436 A1 | 1/2005 | Burch et al. |
| 2005/0020690 A1 | 1/2005 | Burch et al. |
| 2005/0054959 A1 | 3/2005 | Ingimundarson |
| 2005/0054962 A1 | 3/2005 | Bradshaw |
| 2005/0055849 A1 | 3/2005 | Ha |
| 2005/0058734 A1 | 3/2005 | Burch et al. |
| 2005/0059873 A1 | 3/2005 | Glozman et al. |
| 2005/0060910 A1 | 3/2005 | Kaneda et al. |
| 2005/0061332 A1 | 3/2005 | Greenawalt et al. |
| 2005/0063971 A1 | 3/2005 | Jeffers et al. |
| 2005/0070909 A1 | 3/2005 | Egger et al. |
| 2005/0076536 A1 | 4/2005 | Hatfield et al. |
| 2005/0115116 A1 | 6/2005 | Pedersen et al. |
| 2005/0123567 A1 | 6/2005 | First |
| 2005/0158382 A1 | 7/2005 | Cruz et al. |
| 2005/0177084 A1 | 8/2005 | Green et al. |
| 2005/0187071 A1 | 8/2005 | Yamashita et al. |
| 2005/0197711 A1 | 9/2005 | Cachia |
| 2005/0202047 A1 | 9/2005 | Radovic |
| 2005/0208540 A1 | 9/2005 | Shimkets et al. |
| 2005/0228389 A1 | 10/2005 | Stiernborg |
| 2005/0229430 A1 | 10/2005 | Takaba |
| 2005/0229433 A1 | 10/2005 | Cachia |
| 2005/0241187 A1 | 11/2005 | Johnson |
| 2005/0251081 A1 | 11/2005 | McClanahan et al. |
| 2006/0002954 A1 | 1/2006 | Tabata et al. |
| 2006/0015102 A1 | 1/2006 | Toullec et al. |
| 2006/0030854 A1 | 2/2006 | Haines |
| 2006/0058796 A1 | 3/2006 | Hartdegen et al. |
| 2006/0064048 A1 | 3/2006 | Stano |
| 2006/0074434 A1 | 4/2006 | Wenstrom et al. |
| 2006/0079558 A1 | 4/2006 | Aberg et al. |
| 2006/0079559 A1 | 4/2006 | Aberg et al. |
| 2006/0081553 A1 | 4/2006 | Patterson et al. |
| 2006/0148903 A1 | 7/2006 | Burch et al. |
| 2006/0155233 A1 | 7/2006 | Huber et al. |
| 2006/0161090 A1 | 7/2006 | Lee |
| 2006/0162464 A1 | 7/2006 | Hayashi et al. |
| 2006/0178702 A1 | 8/2006 | Pierce et al. |
| 2006/0189914 A1 | 8/2006 | Slavitt |
| 2006/0201011 A1 | 9/2006 | Katsu et al. |
| 2006/0240105 A1 | 10/2006 | Devane et al. |
| 2006/0241066 A1 | 10/2006 | Tomita et al. |
| 2006/0241607 A1 | 10/2006 | Myerson et al. |
| 2006/0241608 A1 | 10/2006 | Myerson et al. |
| 2006/0247566 A1 | 11/2006 | Gobet et al. |
| 2006/0251721 A1 | 11/2006 | Cruz et al. |
| 2006/0258588 A1 | 11/2006 | Pike et al. |
| 2006/0264961 A1 | 11/2006 | Murray-Brown |
| 2006/0269628 A1 | 11/2006 | Burch et al. |
| 2006/0271077 A1 | 11/2006 | Graser |
| 2006/0276737 A1 | 12/2006 | Rose |
| 2006/0282231 A1 | 12/2006 | Kurashina et al. |
| 2007/0010818 A1 | 1/2007 | Stone et al. |
| 2007/0016205 A1 | 1/2007 | Beutter et al. |
| 2007/0016275 A1 | 1/2007 | Ferdinand |
| 2007/0033750 A1 | 2/2007 | Cook et al. |
| 2007/0036876 A1 | 2/2007 | Burch et al. |
| 2007/0051020 A1 | 3/2007 | Tajima et al. |
| 2007/0051376 A1 | 3/2007 | Kulichikhin et al. |
| 2007/0074334 A1 | 4/2007 | Steel |
| 2007/0074426 A1 | 4/2007 | Dorsey |
| 2007/0078518 A1 | 4/2007 | Lavi |
| 2007/0088341 A1 | 4/2007 | Skiba et al. |
| 2007/0094896 A1 | 5/2007 | Hatfield et al. |
| 2007/0128226 A1 | 6/2007 | Radovic |
| 2007/0131798 A1 | 6/2007 | Katsukawa et al. |
| 2007/0141020 A1 | 6/2007 | Barritault et al. |
| 2007/0197948 A1 | 8/2007 | Ingimundarson et al. |
| 2007/0204487 A1 | 9/2007 | Clough |
| 2007/0213296 A1 | 9/2007 | Zhang |
| 2007/0213308 A1 | 9/2007 | Lessem et al. |
| 2007/0214681 A1 | 9/2007 | Dezfouli |
| 2007/0225217 A1 | 9/2007 | Chappell et al. |
| 2007/0225703 A1 | 9/2007 | Schmitz et al. |
| 2007/0260252 A1 | 11/2007 | Schmitz et al. |
| 2007/0265296 A1 | 11/2007 | Dalton et al. |
| 2007/0265634 A1 | 11/2007 | Weinstein |
| 2007/0281906 A1 | 12/2007 | Dalton et al. |
| 2007/0282342 A1 | 12/2007 | Niederberger et al. |
| 2007/0299382 A1 | 12/2007 | Millet |
| 2008/0008777 A1 | 1/2008 | Radovic |
| 2008/0010856 A1 | 1/2008 | Hakkala |
| 2008/0014272 A1 | 1/2008 | Skolnick et al. |
| 2008/0027119 A1 | 1/2008 | Lippa et al. |
| 2008/0041169 A1 | 2/2008 | Walczyk et al. |
| 2008/0057068 A1 | 3/2008 | Dalton et al. |
| 2008/0065224 A1 | 3/2008 | Reigstad et al. |
| 2008/0076829 A1 | 3/2008 | Dalton et al. |
| 2008/0078628 A1 | 4/2008 | Christen |
| 2008/0081834 A1 | 4/2008 | Lippa et al. |
| 2008/0086139 A1 | 4/2008 | Bourke et al. |
| 2008/0086909 A1 | 4/2008 | Raspini |
| 2008/0086913 A1 | 4/2008 | Nawachi et al. |
| 2008/0102121 A1 | 5/2008 | Devane et al. |
| 2008/0113025 A1 | 5/2008 | Devane et al. |
| 2008/0139641 A1 | 6/2008 | Meyer |
| 2008/0141565 A1 | 6/2008 | Rini et al. |
| 2008/0147084 A1 | 6/2008 | Bleich et al. |
| 2008/0153780 A1 | 6/2008 | Meyer |
| 2008/0155731 A1 | 7/2008 | Kasahara |
| 2008/0200989 A1 | 8/2008 | Cachia |
| 2008/0208252 A1* | 8/2008 | Holmes ............... 606/232 |
| 2008/0216593 A1 | 9/2008 | Jacobsen et al. |
| 2008/0217816 A1 | 9/2008 | Hemmi et al. |
| 2008/0221697 A1 | 9/2008 | Graser |
| 2008/0229482 A1 | 9/2008 | Millet |
| 2008/0242646 A1 | 10/2008 | Lessem et al. |
| 2008/0248282 A1 | 10/2008 | Martin et al. |
| 2008/0260791 A1 | 10/2008 | Burch et al. |
| 2008/0262091 A1 | 10/2008 | Burch et al. |
| 2008/0263900 A1 | 10/2008 | Determe et al. |
| 2008/0280975 A1 | 11/2008 | Badul |
| 2008/0282580 A1 | 11/2008 | Ji-Woog |
| 2008/0287406 A1 | 11/2008 | Lessem |
| 2008/0287866 A1 | 11/2008 | Heller |
| 2008/0288019 A1 | 11/2008 | Heller |
| 2008/0294170 A1 | 11/2008 | O'Brien |
| 2008/0301977 A1 | 12/2008 | Roberts et al. |
| 2009/0005358 A1 | 1/2009 | Lessem |
| 2009/0012180 A1 | 1/2009 | Lange et al. |
| 2009/0036893 A1 | 2/2009 | Kartalian et al. |
| 2009/0043318 A1 | 2/2009 | Michel et al. |
| 2009/0054527 A1 | 2/2009 | Burch et al. |
| 2009/0062253 A1 | 3/2009 | Gahman et al. |
| 2009/0062359 A1 | 3/2009 | Burch et al. |
| 2009/0082466 A1 | 3/2009 | Babul |
| 2009/0082773 A1 | 3/2009 | Haines |
| 2009/0082874 A1 | 3/2009 | Cachia |
| 2009/0111792 A1 | 4/2009 | Burch et al. |
| 2009/0113759 A1 | 5/2009 | Heid |

| | | | | | | | |
|---|---|---|---|---|---|---|---|
| 2009/0117167 | A1 | 5/2009 | Burch et al. | JP | 6105859 | A | 4/1994 |
| 2009/0118242 | A1 | 5/2009 | Burch et al. | JP | 7031503 | A | 2/1995 |
| 2009/0133289 | A1 | 5/2009 | Cantoni | JP | 7039559 | A | 2/1995 |
| 2009/0156614 | A1 | 6/2009 | Dalton et al. | JP | 7241307 | A | 9/1995 |
| 2009/0157194 | A1 | 6/2009 | Shikinami | JP | 7255763 | A | 10/1995 |
| 2009/0181098 | A1 | 7/2009 | Garrett et al. | JP | 7308334 | A | 11/1995 |
| 2009/0192222 | A1 | 7/2009 | Yao et al. | JP | 7323039 | A | 12/1995 |
| 2009/0198287 | A1 | 8/2009 | Chiu | JP | 7324202 | A | 12/1995 |
| 2009/0209536 | A1 | 8/2009 | Gahman et al. | JP | 8131477 | A | 5/1996 |
| 2009/0210010 | A1 | 8/2009 | Strnad et al. | JP | 8150162 | A | 6/1996 |
| 2009/0215809 | A1 | 8/2009 | Yao et al. | JP | 8154959 | A | 6/1996 |
| 2009/0216334 | A1 | 8/2009 | Leibel | JP | 8243119 | A | 9/1996 |
| 2009/0222047 | A1 | 9/2009 | Graham | JP | 8299016 | A | 11/1996 |
| 2009/0228049 | A1 | 9/2009 | Park | JP | 9010005 | A | 1/1997 |
| 2009/0287246 | A1 | 11/2009 | Cauldwell et al. | JP | 9010008 | A | 1/1997 |
| 2009/0291975 | A1 | 11/2009 | Stern et al. | JP | 9028409 | A | 2/1997 |
| 2009/0292022 | A1 | 11/2009 | Kowalski et al. | JP | 9051801 | A | 2/1997 |
| 2009/0292023 | A1 | 11/2009 | Kowalski et al. | JP | 9075102 | A | 3/1997 |
| 2009/0306723 | A1 | 12/2009 | Anapliotis et al. | JP | 9140405 | A | 6/1997 |
| 2010/0021107 | A1 | 1/2010 | Naruse et al. | JP | 9191904 | A | 7/1997 |
| 2010/0036430 | A1 | 2/2010 | Hartdegen et al. | JP | 9215501 | A | 8/1997 |
| 2010/0152752 | A1 | 6/2010 | Denove | JP | 9276308 | A | 10/1997 |
| 2011/0118780 | A1 | 5/2011 | Holmes, Jr. | JP | 9313207 | A | 12/1997 |
| 2011/0178557 | A1 | 7/2011 | Rush et al. | JP | 10043224 | A | 2/1998 |
| 2011/0224729 | A1 | 9/2011 | Baker et al. | JP | 10052472 | A | 2/1998 |
| 2011/0301648 | A1 | 12/2011 | Lofthouse et al. | JP | 10155505 | A | 6/1998 |
| 2012/0071935 | A1 | 3/2012 | Keith et al. | JP | 10155507 | A | 6/1998 |
| | | | | JP | 10155509 | A | 6/1998 |
| FOREIGN PATENT DOCUMENTS | | | | JP | 10155512 | A | 6/1998 |
| | | | | JP | 10168608 | A | 6/1998 |
| EP | 60353 | A1 | 9/1982 | JP | 10234759 | A | 9/1998 |
| EP | 284922 | A2 | 10/1988 | JP | 10328219 | A | 12/1998 |
| EP | 491983 | A1 | 7/1992 | JP | 11012803 | A | 1/1999 |
| EP | 557409 | A1 | 9/1993 | JP | 11032805 | A | 2/1999 |
| EP | 649447 | A1 | 4/1995 | JP | 11056408 | A | 3/1999 |
| EP | 679377 | A2 | 11/1995 | JP | 11076283 | A | 3/1999 |
| EP | 757545 | A1 | 2/1997 | JP | 11146802 | A | 6/1999 |
| EP | 796603 | A1 | 9/1997 | JP | 11169201 | A | 6/1999 |
| EP | 991404 | A1 | 4/2000 | JP | 11192103 | A | 7/1999 |
| EP | 1044618 | A1 | 10/2000 | JP | 11276203 | A | 10/1999 |
| EP | 1056364 | A1 | 12/2000 | JP | 11276208 | A | 10/1999 |
| EP | 1113768 | A1 | 7/2001 | JP | 11279803 | A | 10/1999 |
| EP | 891160 | B1 | 10/2001 | JP | 11315401 | A | 11/1999 |
| EP | 679377 | B1 | 8/2002 | JP | 11318511 | A | 11/1999 |
| EP | 1287787 | A1 | 3/2003 | JP | 2000060934 | A | 2/2000 |
| EP | 995364 | B1 | 6/2003 | JP | 2000093486 | A | 4/2000 |
| EP | 1307116 | B1 | 5/2005 | JP | 2000116686 | A | 4/2000 |
| EP | 1531741 | A1 | 5/2005 | JP | 2000116696 | A | 4/2000 |
| EP | 1618806 | A1 | 1/2006 | JP | 2000116698 | A | 4/2000 |
| EP | 1691830 | A1 | 8/2006 | JP | 2000232901 | A | 8/2000 |
| EP | 1715888 | A2 | 11/2006 | JP | 2000287705 | A | 10/2000 |
| EP | 1464281 | B1 | 12/2006 | JP | 2000308654 | A | 11/2000 |
| EP | 1446028 | B1 | 1/2007 | JP | 2000316603 | A | 11/2000 |
| EP | 1772123 | A1 | 4/2007 | JP | 2000325376 | A | 11/2000 |
| EP | 1792577 | A1 | 6/2007 | JP | 2000328304 | A | 11/2000 |
| EP | 1800555 | A1 | 6/2007 | JP | 2001000463 | A | 1/2001 |
| EP | 1806062 | A1 | 7/2007 | JP | 2001029374 | A | 2/2001 |
| EP | 1513561 | B1 | 9/2007 | JP | 2001087297 | A | 4/2001 |
| EP | 1836981 | A2 | 9/2007 | JP | 2001095828 | A | 4/2001 |
| EP | 1885309 | A2 | 2/2008 | JP | 2001104008 | A | 4/2001 |
| EP | 1913831 | A1 | 4/2008 | JP | 2001140102 | A | 5/2001 |
| EP | 1927322 | A1 | 6/2008 | JP | 2001269367 | A | 10/2001 |
| EP | 1587506 | B1 | 7/2008 | JP | 2001299404 | A | 10/2001 |
| EP | 1952776 | A1 | 8/2008 | JP | 2001299792 | A | 10/2001 |
| FR | 2893496 | A1 | 5/2007 | JP | 2001353005 | A | 12/2001 |
| FR | 2916954 | A1 | 12/2008 | JP | 2001355155 | A | 12/2001 |
| GB | 2023404 | A | 1/1980 | JP | 2002000302 | A | 1/2002 |
| GB | 2228202 | A | 8/1990 | JP | 2002052034 | A | 2/2002 |
| GB | 2337446 | A | 11/1999 | JP | 2002065712 | A | 3/2002 |
| GB | 2425961 | A | 11/2006 | JP | 2002165611 | A | 6/2002 |
| GB | 2269753 | A | 2/1994 | JP | 2002209610 | A | 7/2002 |
| JP | 2071704 | A | 3/1990 | JP | 2002209931 | A | 7/2002 |
| JP | 2295572 | A | 12/1990 | JP | 2002282011 | A | 10/2002 |
| JP | 3188849 | A | 8/1991 | JP | 2002345501 | A | 12/2002 |
| JP | 4108401 | A | 4/1992 | JP | 2002355105 | A | 12/2002 |
| JP | 4129550 | A | 4/1992 | JP | 2003000629 | A | 1/2003 |
| JP | 5329005 | A | 12/1993 | JP | 2003033204 | A | 2/2003 |
| JP | 6054702 | A | 3/1994 | JP | 2003052728 | A | 2/2003 |
| JP | 6054872 | A | 3/1994 | JP | 2003126130 | A | 5/2003 |
| JP | 6062906 | A | 3/1994 | | | | |

| | | | |
|---|---|---|---|
| JP | 2003210206 A | 7/2003 |
| JP | 2003250601 A | 9/2003 |
| JP | 2003319804 A | 11/2003 |
| JP | 2004166810 A | 6/2004 |
| JP | 2004167069 A | 6/2004 |
| JP | 2004167144 A | 6/2004 |
| JP | 2004180746 A | 7/2004 |
| JP | 2004201933 A | 7/2004 |
| JP | 2004202074 A | 7/2004 |
| JP | 2004202128 A | 7/2004 |
| JP | 2004215870 A | 8/2004 |
| JP | 2004216087 A | 8/2004 |
| JP | 2004229992 A | 8/2004 |
| JP | 2004242988 A | 9/2004 |
| JP | 2004250796 A | 9/2004 |
| JP | 2004329452 A | 11/2004 |
| JP | 2005000347 A | 1/2005 |
| JP | 2005009011 A | 1/2005 |
| JP | 2005013682 A | 1/2005 |
| JP | 2005021191 A | 1/2005 |
| JP | 2005040571 A | 2/2005 |
| JP | 2005042213 A | 2/2005 |
| JP | 2005052593 A | 3/2005 |
| JP | 2005152218 A | 6/2005 |
| JP | 2005160560 A | 6/2005 |
| JP | 2005245471 A | 9/2005 |
| JP | 2005245571 A | 9/2005 |
| JP | 2005279188 A | 10/2005 |
| JP | 2005281917 A | 10/2005 |
| JP | 2005287726 A | 10/2005 |
| JP | 2005305063 A | 11/2005 |
| JP | 2005305085 A | 11/2005 |
| JP | 2005349225 A | 12/2005 |
| JP | 2006000403 A | 1/2006 |
| JP | 2006000549 A | 1/2006 |
| JP | 2006043369 A | 2/2006 |
| JP | 2006043376 A | 2/2006 |
| JP | 2006055591 A | 3/2006 |
| JP | 2006081797 A | 3/2006 |
| JP | 2006130248 A | 5/2006 |
| JP | 2006132037 A | 5/2006 |
| JP | 2006141651 A | 6/2006 |
| JP | 2006187545 A | 7/2006 |
| JP | 2006247335 A | 9/2006 |
| JP | 2006249623 A | 9/2006 |
| JP | 2006263407 A | 10/2006 |
| JP | 2006271915 A | 10/2006 |
| JP | 2006288491 A | 10/2006 |
| JP | 2006289003 A | 10/2006 |
| JP | 2006314656 A | 11/2006 |
| JP | 2006326264 A | 12/2006 |
| JP | 2007090017 A | 4/2007 |
| JP | 2007097846 A | 4/2007 |
| JP | 2007130369 A | 5/2007 |
| JP | 2007167180 A | 7/2007 |
| JP | 2007215967 A | 8/2007 |
| JP | 2007229378 A | 9/2007 |
| JP | 2007236905 A | 9/2007 |
| JP | 2007244786 A | 9/2007 |
| JP | 2007252585 A | 10/2007 |
| JP | 2007313043 A | 12/2007 |
| JP | 2007319201 A | 12/2007 |
| JP | 2007330743 A | 12/2007 |
| JP | 2008000244 A | 1/2008 |
| JP | 2008023258 A | 2/2008 |
| JP | 2008023300 A | 2/2008 |
| JP | 2008061960 A | 3/2008 |
| JP | 2008093399 A | 4/2008 |
| JP | 2008121177 A | 5/2008 |
| WO | WO8504558 A1 | 10/1985 |
| WO | WO8901745 A1 | 3/1989 |
| WO | WO9211777 A1 | 7/1992 |
| WO | WO9401496 A1 | 1/1994 |
| WO | WO9528887 A1 | 11/1995 |
| WO | WO9629988 A1 | 10/1996 |
| WO | WO9641523 A1 | 12/1996 |
| WO | WO9721404 A1 | 6/1997 |
| WO | WO9735528 A1 | 10/1997 |
| WO | WO9858631 A1 | 12/1998 |
| WO | WO9943227 A1 | 9/1999 |
| WO | WO0006036 A1 | 2/2000 |
| WO | WO0015163 A1 | 3/2000 |
| WO | WO 00/18313 | 4/2000 |
| WO | WO0121119 A1 | 3/2001 |
| WO | WO0191674 A1 | 12/2001 |
| WO | WO0211573 A1 | 2/2002 |
| WO | WO0217840 A1 | 3/2002 |
| WO | WO0241944 A2 | 5/2002 |
| WO | WO02098254 A1 | 12/2002 |
| WO | WO03045179 A2 | 6/2003 |
| WO | WO03099144 A1 | 12/2003 |
| WO | WO03099344 A2 | 12/2003 |
| WO | WO2004056305 A2 | 7/2004 |
| WO | WO2004058286 A1 | 7/2004 |
| WO | WO2004069866 A1 | 8/2004 |
| WO | WO2004078220 A2 | 9/2004 |
| WO | WO2004107895 A1 | 12/2004 |
| WO | WO2005013745 A1 | 2/2005 |
| WO | WO2005034670 A2 | 4/2005 |
| WO | WO2005039439 A2 | 5/2005 |
| WO | WO2005056050 A1 | 6/2005 |
| WO | WO2005079828 A2 | 9/2005 |
| WO | WO2005102092 A1 | 11/2005 |
| WO | WO2006030546 A1 | 3/2006 |
| WO | WO2006047227 A1 | 5/2006 |
| WO | WO2006058140 A2 | 6/2006 |
| WO | WO2006066419 A1 | 6/2006 |
| WO | WO2006069451 A1 | 7/2006 |
| WO | WO2006069452 A1 | 7/2006 |
| WO | WO2006088412 A1 | 8/2006 |
| WO | WO2006107779 A2 | 10/2006 |
| WO | WO2006120385 A2 | 11/2006 |
| WO | WO2007008348 A2 | 1/2007 |
| WO | WO2007021865 A2 | 2/2007 |
| WO | WO2007025520 A1 | 3/2007 |
| WO | WO2007089617 A2 | 8/2007 |
| WO | WO2007098057 A2 | 8/2007 |
| WO | WO2007106498 A2 | 9/2007 |
| WO | WO2008006929 A1 | 1/2008 |
| WO | WO2008102405 A1 | 8/2008 |
| WO | WO2008118426 A1 | 10/2008 |
| WO | WO 2009/018527 | 2/2009 |
| WO | WO 2010/093696 | 8/2010 |

OTHER PUBLICATIONS

Mini TightRope™ for Hallux Valgus Correction and Lisfranc Ligament Repair Surgical Technique, Anthrex, copyright 2007, 6 pp.

H. Kelikian, M.D., "Miscellaneous Methods", Hallux Valgus, Allied Deformities of the Forefoot and Metatarsalgia, 1965, pp. 253-261, W.B. Saunders Company, Philadelphia and London.

International Search Report and Written Opinion issued in PCT/US2010/023757, mailed Jun. 2, 2010, 16 page.

International Search Report and Written Opinion issued in PCT/US2011/039041, mailed Oct. 19, 2011, 14 pages.

Coughlin et al., "Proximal metatarsal osteotomy and distal soft tissue reconstruction as treatment for hallux valgus deformity", Keio J. Med. 54(2) p. 60-65.

RetroButton™ ACL Reconstruction, Arthrex® 8 pages, ©Copyright Arthrex Inc., 2007.

Mini TightRope® Surgical Technique, © Copyright 2007, 6 pages.

International Search Report and Written Opinion issued in PCT/US2010/049583, mailed Dec. 10, 2010, 13 pages.

* cited by examiner

-PRIOR ART-

-PRIOR ART-

METHODS AND DEVICES FOR TREATING A STRUCTURAL BONE AND JOINT DEFORMITY

FIELD OF THE INVENTION

The various embodiments disclosed herein relate to methods and devices for treating a structural bone and joint deformity. More specifically, certain embodiments relate to systems and methods for correcting such deformity, including hallux valgus.

BACKGROUND OF THE INVENTION

Hallux valgus deformities in the human foot typically relate to at least one of two conditions: a deviated position of the great toe where the great toe leans in towards the second toe, and a deviation in the angle between the first and second metatarsal bones of the foot. The most commonly used medical terms associated with these deformities are "hallux valgus" and "hallux abducto valgus," where "hallux" refers to the great toe, "valgus" refers to the abnormal slant of the great toe, and "abducto" refers to the abnormal slant or leaning of the great toe towards the second toe, as shown in FIGS. 1A and 1B.

There are generally four stages in the development of hallux abducto valgus ("HAV"). Stage one involves a lateral shift of the entire hallux upon the first metatarsal head. Stage two relates to abduction of the hallux. In stage three, because abduction of the hallux displaces the long flexor and extensor tendons laterally, contraction of these muscles during the propulsive period produces a retrograde medially directed component of force as the proximal phalanx pushes the first metatarsal bone in an adducted position. Finally, stage four involves complete dislocation of the first MPJ, which rarely occurs without underlying rheumatic inflammatory disease or neuromuscular disorder. In some situations, HAV may lead to the formation of a bunion. "Bunion" refers to the pathological bump, callous, and/or inflammation on the side of the great toe joint associated with either a bursal sac or structural deformity of the great toe as described above.

The abnormalities associated with development of hallux valgus as described above are caused by a biomechanical abnormality, where certain tendons, ligaments, and supportive structures of the first metatarsal are no longer functioning correctly. While the underlying mechanisms are not fully understood, this biomechanical abnormality may be due to the structure of the foot (such as flat feet, excessive ligamentous flexibility, or abnormal bone structure), certain neurological conditions, poor-fitting footwear, or just chronic "wear and tear" leading to a progression of initially small irregularities.

Various treatments for hallux valgus and/or bunions exist. Various surgical procedures may address some combination of removing the abnormal bony enlargement of the first metatarsal bone, realigning portions of the first metatarsal bone relative to the adjacent metatarsal bone, straightening the first metatarsal bone relative to the adjacent toes through manipulations of the joint capsule, realigning the cartilagenous surfaces of the great toe joint, and/or repositioning the sesamoid bones beneath the first metatarsal bone. Further treatments can include bunion pads and external splints. All of these known treatments have shortcomings in either effectiveness (pads and splints) or invasiveness (the surgical procedures). With respect to the existing surgical procedures, the vast majority require an osteotomy for realignment of portions of the first metatarsal bone, which leads to long recovery and the need for patients to wear a cast or surgical boot for weeks following the operation. Further, the surgical patients are left with a significant scar and poor cosmesis. In addition, studies have highlighted that as many as 30% of bunion surgery patients are unhappy with the result and nearly 10% have post-surgical complications. Finally, the surgical procedures are costly, requiring anesthesia, a lengthy operating time, and multiple trained medical staff.

BRIEF SUMMARY OF THE INVENTION

One embodiment disclosed herein relates to an implantable system for treating a bone deformity. The system includes a drill guide, a flexible band guide, a drill, an implantation cannula, and a locking component. The drill guide has a guide tube, an arm coupled to the tube, and a seat configured to be positioned against a first bone. The flexible band guide has a first arm coupled to the arm of the drill guide and a second arm coupled to the first arm that has a flexible band receiving component. The implantation cannula defines a tube configured to be inserted through a hole in the first bone and further configured to receive the flexible band.

Another embodiment relates to a method of treating a bone deformity. The method includes positioning a drill guide against a first bone, coupling a tension band guide to the drill guide, drilling a hole through the first bone, inserting an implantation cannula through the drill guide, inserting a tension band through the implantation cannula and into contact with the tension band guide, and locking the tension band in place with a locking mechanism.

A further embodiment relates to a method of reducing an intermetatarsal angle. The method includes surgically reducing the intermetatarsal angle of a first metatarsal bone, drilling a hole through the bone, inserting a leader component couple to a flexible band through the hole, advancing the leader component around a second metatarsal bone and back through the hole, detaching the leader component from the flexible band, and securing the first end of the flexible band against the second end.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Various embodiments disclosed herein relate to methods and devices for treating a bone deformity, such as, for example, hallux valgus (bunions). More specifically, various embodiments herein relate to tightening or connection systems and methods for coupling two bones such as the first and second metatarsal bones to correct structural deformity. Certain implementations relate to methods and one or more devices for correcting the deformity and subsequently implanting a flexible device that retains the first metatarsal bone in its corrected (non-deviated) position. In these implementations, the structural deformity of the bone(s) and associated joint(s) is corrected in the surgical setting and then the flexible device is implanted to maintain the corrected position of the bone(s). The flexible device, in certain embodiments as described in detail below, is inserted through a hole drilled in the first metatarsal bone and positioned around the second metatarsal bone, thereby avoiding the necessity of drilling a hole in the second metatarsal bone. A "flexible band," "flexible component," "flexible mechanism," or "flexible device" as described herein is a component or mechanism—such as, for example, a band—that exhibits flexible characteristics and maintains or retains the first metatarsal bone in the corrected or normal (non-deviated) position. It is understood that, in certain embodiments, the implanted device can be a tension band as described below.

Alternative embodiments provide for slow correction of the deformity. That is, these embodiments relate to methods and devices used to implant a tension device that can apply a tightening force that urges the first and second metatarsal bones together, thereby providing a slow correction of the deformity by decreasing the metatarsal bone angle over time without requiring the acute damage to the bones or tendons of the foot such as that created by an osteotomy. A device that applies a "tightening force" or a "dynamic tightening force" is a device that allows for the first metatarsal bone to be repositioned toward its normal (non-deviated) position while continuing to apply a corrective force as the first metatarsal bone moves toward a corrected position. That is, a "tension band," "tension device," "tension component," "tension mechanism," "dynamic tension component," or "dynamic tension mechanism" as described herein is a flexible component or mechanism—such as, for example, a band—that not only exhibits flexibility characteristics, but also applies a corrective force intended to result in the gradual repositioning of the first metatarsal bone toward its normal (non-deviated) position.

As such, various embodiments disclosed herein provide systems and methods for implantation of treatment devices and treatment of hallux valgus with reduced trauma and quicker recovery in comparison to known systems and treatments.

Figure 1A:
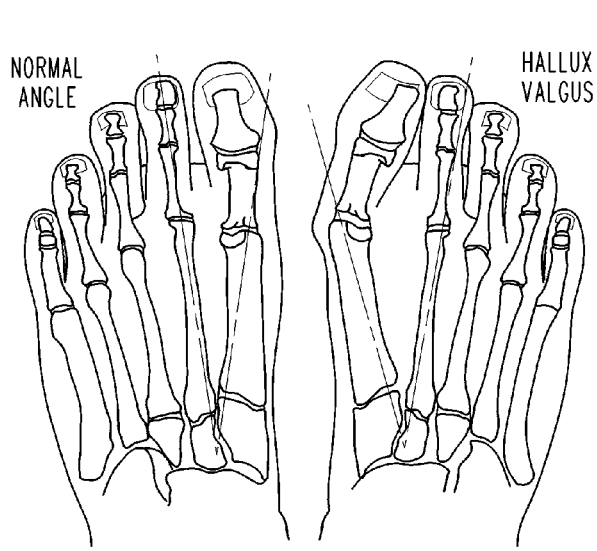
FIG. 1A is a schematic depiction of a healthy foot and a foot exhibiting hallux valgus.
Figure 1B:
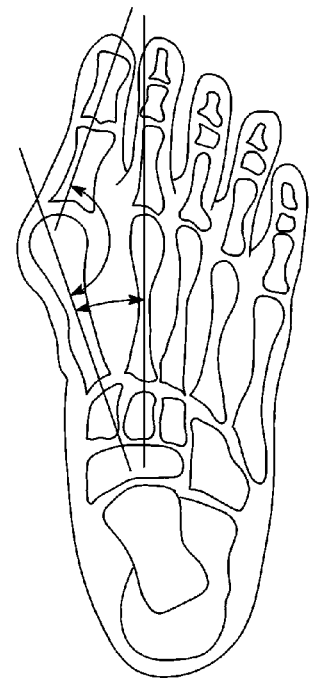
FIG. 1B is a schematic depiction of a second foot exhibiting hallux valgus.
Figure 2:
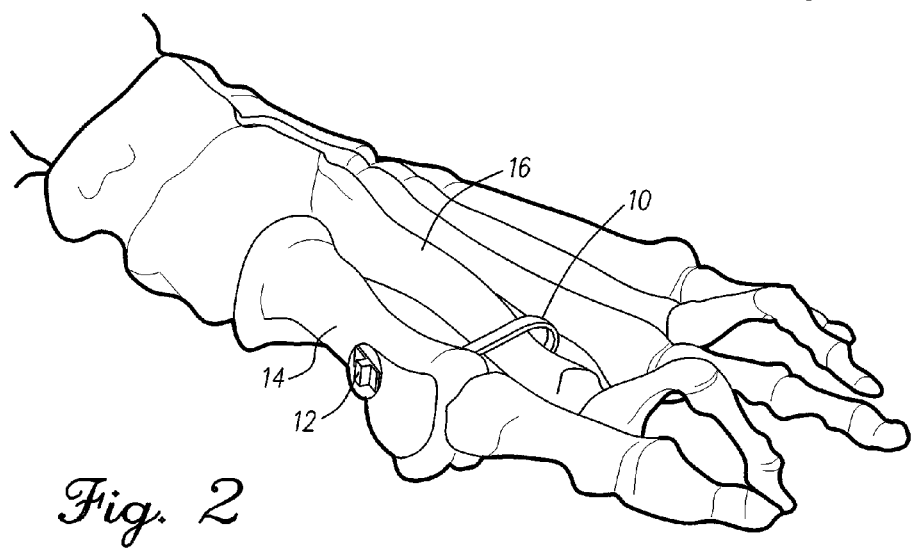
FIG. 2 is a perspective view of an implantable bone deformity treatment device in a foot exhibiting hallux valgus, according to one embodiment.

FIG. 2 depicts an implanted flexible device 10 configured to maintain the surgically corrected position of the first metatarsal bone 14, according to one embodiment. In this figure, the device 10 is a single flexible band disposed through a hole (not shown) in the first metatarsal 14 and around the second metatarsal 16. The two ends of the band 10 are secured with a locking mechanism 12 positioned against the first metatarsal bone 14 at the hole. The locking mechanism 12 can take a variety of forms, including several discussed below. The flexible band 10 in this implementation is a single flexible band 10, as will be described in further detail herein. Alternatively, the device 10 is a tension band configured to maintain the corrected position of the first metatarsal 14 by continuing to apply force. It is understood that various tension device embodiments disclosed in U.S. application Ser. No. 12/371,354, entitled "Methods and Devices for Treating Hallux Valgus" and filed on Feb. 13, 2009, which is hereby incorporated by reference in its entirety, could be used with the methods, systems, and devices disclosed herein. It is also understood that each of the various device and method embodiments disclosed herein can be the sole treatment for the bone deformity. It is further understood that any of these embodiments could also be used in conjunction with any one or more of other known treatments, such as surgical remodeling of the bones, surgical removal of the underlying bunion, surgical releasing or tightening of adjacent soft tissues, treatment with pads, splints, or any other treatment method or device. In addition, it is understood that the methods, systems, and devices disclosed herein can be used to treat structural deformity in other metatarsal bones or other areas of the human body or even such deformity in other animals.

In certain embodiments, the flexible band 10 exhibits elasticity. "Elasticity" is the physical property of a material that deforms under stress (e.g. external forces), but returns to its original shape when the stress is removed. The amount of deformation is called the strain. In certain alternative implementations, the flexible band 10 does not exhibit substantial elasticity. In further embodiments in which the flexible band is a tension band, the tension band can exhibit elasticity. That is, a tension band can be urged into a deformed or strained configuration and then, as a result of the component's elasticity, will apply a force as the component returns to its original shape.

According to one alternative embodiment in which the component 10 shown in FIG. 2 is an elastic tension band 10 for slow correction of the structural deformity, the elastic band 10 is configured to apply a force urging the first metatarsal bone 14 and second metatarsal bone 16 toward each other as the component 10 returns from its tensioned state (in which it has been deformed) to its untensioned state or original shape, as described above. In one embodiment, the elastic tension band 10 is configured to have an untensioned (or original) length such that, when initially positioned during surgery as shown through the hole in the first metatarsal 14 and around the second metatarsal 16, the component 10 is configured to be tensioned (or deformed) such that the component 10 applies a force pulling the two bones together and continues to apply that force even as the two bones get closer together. In addition, the elastic band 10 may be further configured such that as the two metatarsal bones are slowly pulled together over time—thereby treating the hallux valgus—the elastic band 10 reaches its untensioned length when the first metatarsal is urged inward so far that the hallux valgus is fully or at least partly treated or corrected. Alternatively, the elastic band 10 may be configured such that its untensioned length is not reached when the hallux valgus is fully treated. For example, the elastic band 10 may be configured to remain in a tensioned state even after the hallux valgus has been fully treated in order to maintain the first metatarsal in the correct position in relation to the second metatarsal. It is understood that, according to certain embodiments, the force decreases as the first metatarsal bone moves toward the second metatarsal bone.

According to one implementation in which the component 10 is an elastic band 10, the component 10 is configured such that the change from the tensioned length to the untensioned length constitutes a change of at least 10% from the tensioned length. Alternatively, the change from the tensioned to the untensioned length constitutes a change of at least 25% in the length. In a further embodiment, the amount of change constitutes a change of at least 50%.

Figure 3:
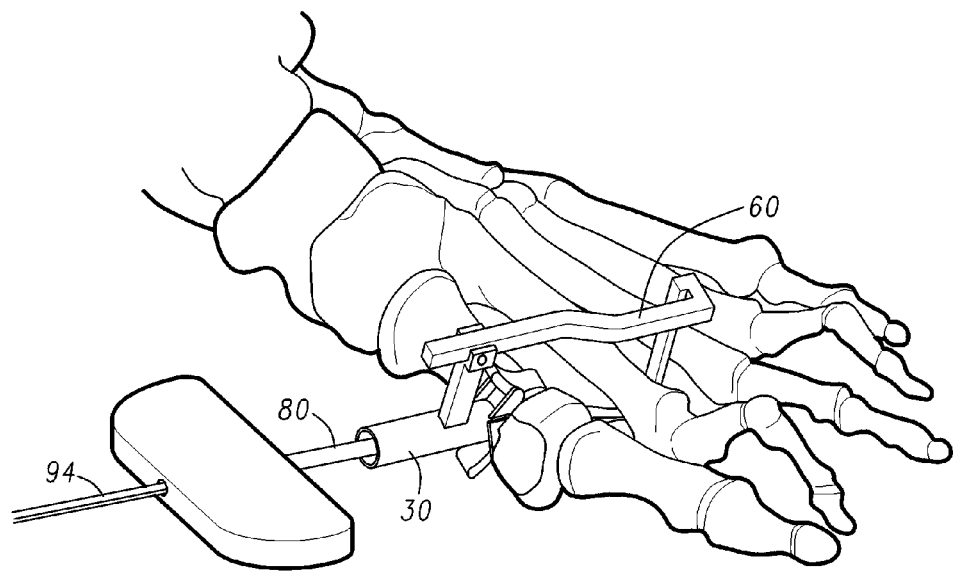
FIG. 3 is a perspective view of a drill guide, a flexible band guide, and an implantation cannula positioned on a foot for implantation of an implantable flexible band, according to one embodiment.

The various flexible and tension bands described herein can be implanted using various implantation systems and procedures, including those described herein. While the various implanted components discussed below will refer to flexible bands, it is understood that tension bands can be implanted in the same manner using the same procedures and devices. In one exemplary system as shown in FIG. 3 and described in further detail below according to various implementations, a flexible band 94 can be implanted using various steps that include the use of a drill guide 30, a flexible band guide 60, and an implantation cannula 80.

Figure 4:
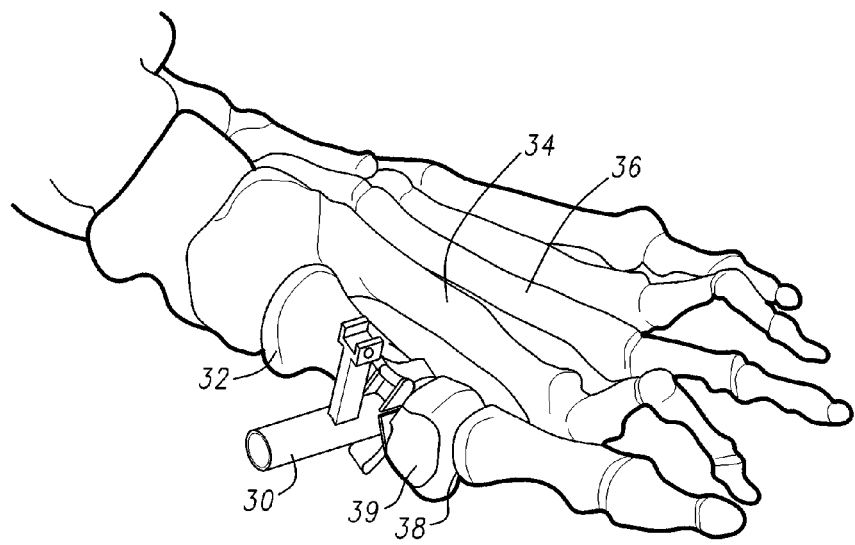
FIG. 4 is a perspective view of a drill guide positioned against a first metatarsal bone, according to one embodiment.

An implantation procedure in accordance with one implementation includes creating an incision along the forefoot adjacent to the big toe (for purposes of positioning the drill guide and drilling the hole) and then positioning the drill guide 30 against the first metatarsal bone 32 as shown in FIG. 4. According to one embodiment, the bone 32 is accessed via a small medial incision at the preferred location along the bone 32. Alternatively, the bone 32 can be access via an incision over the first metatarsal-phalangeal joint ("MTP joint") 38 and the first metatarsal bone 32. In a further alternative, the bone 32 can be accessed via any known procedure or incision location to gain access for purposes of drilling a hole in the first metatarsal 32.

Continuing with FIG. 4, in one embodiment, the drill guide 30 is positioned on the medial side and directed laterally with its longitudinal axis generally perpendicular to the medial surface of the first metatarsal 32 such that the longitudinal axis of the guide 30, if it were extended, would generally intersect with the longitudinal axes of both the first and second metatarsal bones 32, 34. According to certain implementations, the guide 30 is positioned near the distal end of the first metatarsal bone 32. Alternatively, if the joint capsule of the MTP joint 38 has been opened on the medial side of the bone 32 (for example to perform an adjunctive removal of any "eminence," which can result in a relatively flat surface 39 along the bone 32 as shown), the drill guide 30 can be positioned against the flat surface 39 of the first metatarsal 32 within the opened joint capsule.

Figure 5:
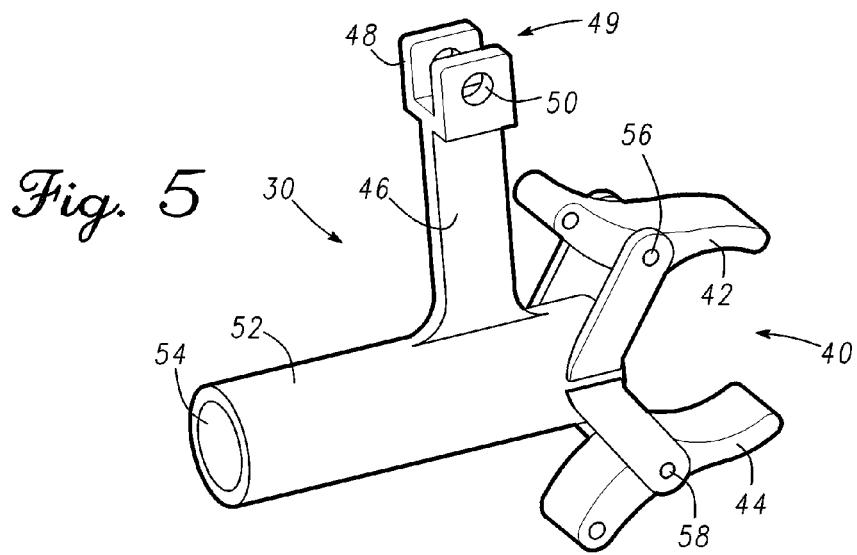
FIG. 5 is a perspective view of a drill guide, according to one embodiment.

A detailed depiction of the drill guide 30 of this embodiment is shown in FIG. 5. The drill guide 30 has a tube 52 having a lumen 54 that is configured to receive at least a drill as described in further detail below. In some embodiments, the lumen 54 is also configured to receive an implantation cannula and/or other devices or components used for implantation of a hallux valgus treatment device such as those disclosed herein.

The drill guide 30 has a seat 40 that is structured to be positioned against or in contact with the first metatarsal bone 32 as shown in FIG. 4 such that the bone 32 is seated in, seated adjacent to, or positioned against the seat 40. The seat 40 is coupled to or positioned with respect to the tube 52 and defines an opening (not shown) in communication with the lumen 54 of the tube 52 such that any object inserted into the proximal end of the tube 52 will exit the distal end of the tube 52 at the opening defined in the seat 40. In this implementation, the seat 40 is an arcuate, open socket-like structure 40 having a first pivotal arm 42 and a second pivotal arm 44, both of which are configured to be positioned against or adjacent to opposing sides (or the top and bottom) of a bone. In one embodiment, the arms 42, 44 are coupled to the guide 30 at joints 56, 58 and can pivot at those joints 56, 58. The pivotal arms 42, 44 are configured to pivot between an "open" position in which the arms 42, 44 are positioned farther apart from each other such that the seat 40 is bigger and a "closed" position in which the arms 42, 44 are positioned closer together, resulting in the seat 40 being smaller. According to one implementation, the pivotal arms 42, 44 are initially positioned in the "open" position prior to positioning the guide 30 in relation to the first metatarsal bone 32, and when the guide 30 has been properly positioned, the arms 42, 44 are moved to the "closed position" such that the arms 42, 44 are in contact with the bone 32, thereby providing some stabilization of the guide 30 with respect to the bone 32. In a further embodiment, the pivotal arms 42, 44 are tensioned such that a force is applied to the arms 42, 44 urging them toward the "closed" position. In this embodiment, the arms 42, 44 must be urged into and held in the "open" position and then positioned around the bone 32 and then the arms 42, 44 are released, thereby allowing the arms 42, 44 to be urged into the "closed" position around the bone 32. According to one implementation, the arms 42, 44 are tensioned with spring components (not shown) coupled to the arms 42, 44. Alternatively, the arms 42, 44 are tensioned using any known mechanism or component. Alternatively, the arms 42, 44 are not pivotal. In a further alternative, the seat 40 can be any structure positioned on or near the distal end of the tube 52 and configured to be positioned against or placed in contact with a bone.

According to one embodiment, the drill guide 30 also has an arm 46 having a coupling component 48. In the embodiment depicted in FIG. 5, the coupling component 48 includes a slot 49 configured to receive and secure another arm. The slot 49 has a hole 50 configured to receive a pin (not shown) to lock the second arm in place in the slot 49. Alternatively, the coupling component 48 can be any structure configured to couple the arm 46 to a second arm or guide component as will be described in further detail below. In a further alternative, the guide 30 has no such arm or coupling component.

Figure 6:
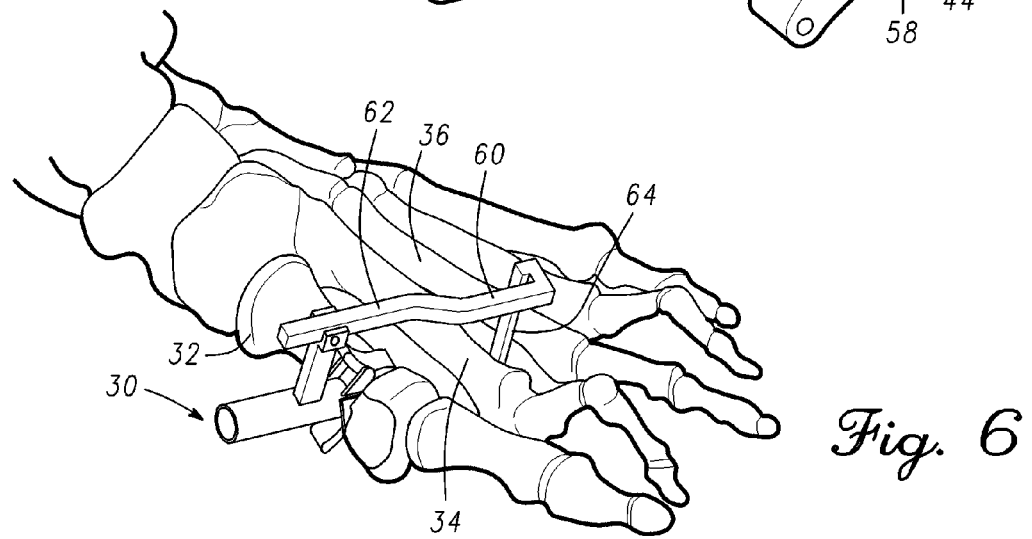
FIG. 6 is a perspective view of a drill guide and a flexible band guide positioned on a foot, according to one embodiment.
Figure 7:
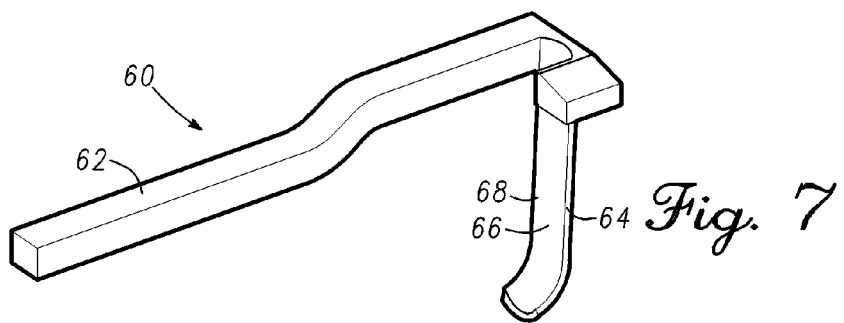
FIG. 7 is a perspective view of a flexible band guide, according to one embodiment.

As shown in FIG. 6, the next step according to one embodiment of the implantation procedure is to position the flexible band guide 60 with respect to the drill guide 30 and the patient's foot. As best shown in FIG. 7, the guide 60 has a first arm 62 and a second arm 64. The user couples the first arm 62 to the coupling component 48 of the drill guide 30 and further positions the guide 60 such that the second arm 64 is positioned between the second metatarsal bone 34 and the third metatarsal bone 36. In one embodiment, the flexible band guide 60 is positioned by first creating a small incision (sometimes referred to as a "stab" incision) between the second and third metatarsal bones 34, 36 and then inserting the second arm 64 into the incision.

As shown in FIG. 7, the second arm 64 of the guide 60 has a receiving component 66 and defines a track 68 along the side of the arm 64 facing the second metatarsal bone 34. As described in further detail below, the receiving component 66 as shown is an arcuate end 66 that is configured to receive the leader component and/or the flexible band (as described in further detail below) and direct the component along the track 68 during implantation. In alternative embodiments, the receiving component 66 can be any structure configured to be capable of receiving a flexible band during implantation.

Figure 8:
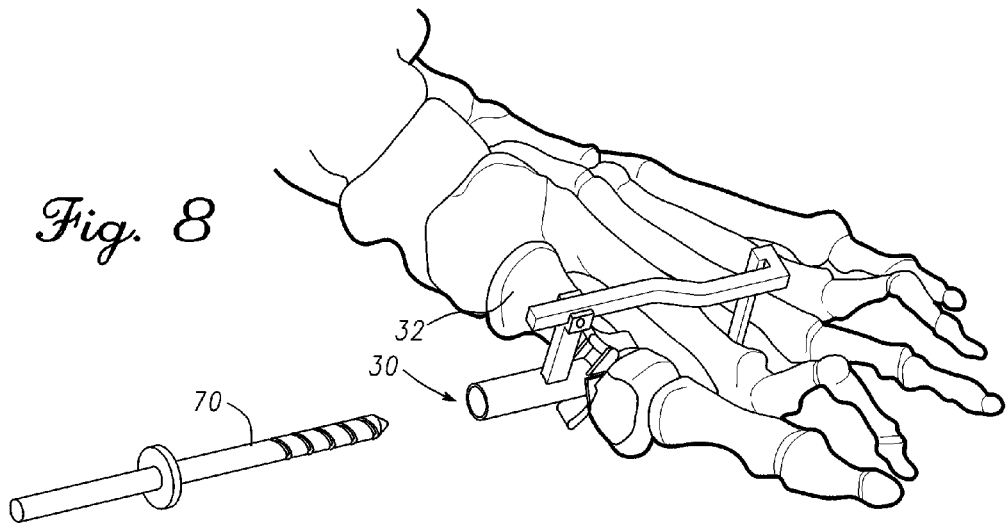
FIG. 8 is a perspective view of a drill being inserted into a drill guide positioned against a first metatarsal bone, according to one embodiment.

According to one embodiment as shown in FIG. 8, the next step in the implantation procedure is drilling a hole in the first metatarsal bone 32. In this step, the drill 70 is inserted through the properly positioned drill guide 30, which can provide some stability and guidance for drilling the hole in the bone. When the drill 70 has drilled a hole through the first metatarsal bone 32, the drill 70 is removed.

Figure 9:
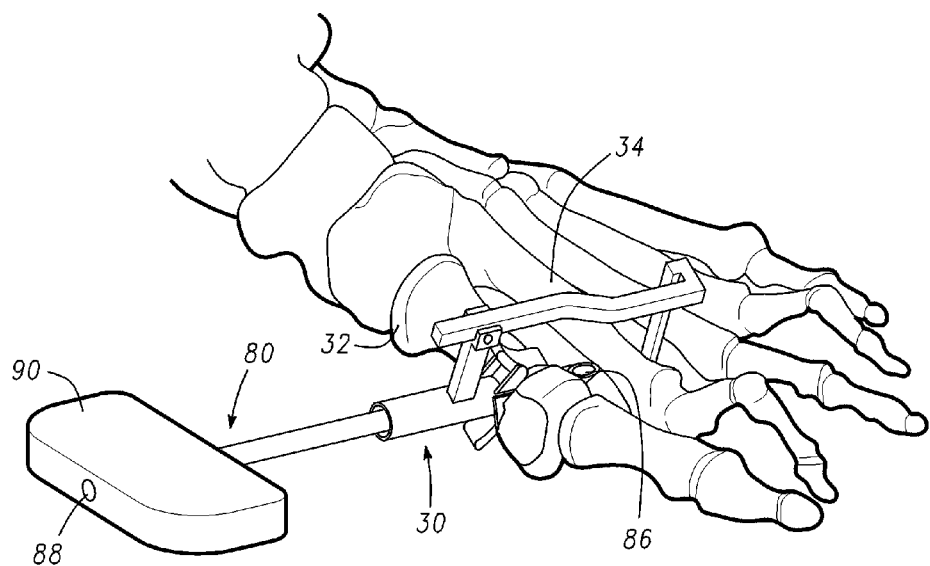
FIG. 9 is a perspective view of an implantation cannula being inserted into a drill guide positioned against a first metatarsal bone, according to one embodiment.
Figure 10:
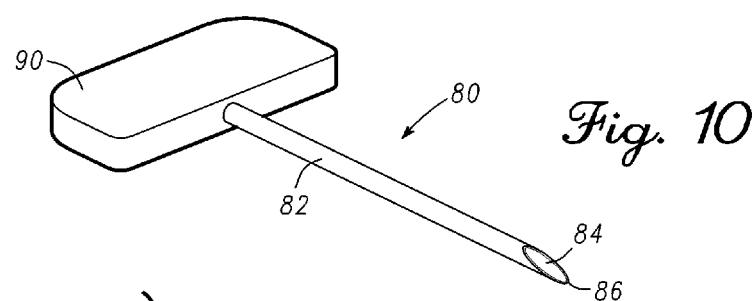
FIG. 10 is a perspective view of an implantation cannula, according to one embodiment.

Subsequently, an implantation cannula 80 is inserted through the drill guide 30 and thus through the newly formed hole (not shown) in the first metatarsal bone 32, as shown in FIG. 9 according to one implementation. More specifically, according to one embodiment, the cannula 80 is inserted through the drill tube 30 and positioned under the second metatarsal bone 34 as depicted in FIG. 9 but, according to one implementation, above the flexor tendons (not shown). As best shown in FIG. 10, the cannula 80, in accordance with one embodiment, has a tip 86 that is canted, resulting in a sharp end to facilitate insertion. When the cannula 80 is inserted under the second bone 34, the opening in the tip 86 faces upward (toward the underside of the second metatarsal bone 34). This positioning can be accomplished by initially directing the cannula 80 toward the second metatarsal 34 until the bone 34 is felt tactilely by the operator via the cannula 80. Then the cannula 80 can be further manipulated by the operator as necessary to properly position the tip 86 adjacent the bottom surface of the second metatarsal bone 34 and further adjacent to the receiving component 66 of the second arm 64 of the flexible band guide 60. Alternatively, the cannula 80 can be positioned through the drill guide 30 and under the second metatarsal bone 34 by any known method.

As best shown in FIG. 10, the implantation cannula 80 of this embodiment has a tube 82 defining a lumen 84, a tip 86 at the distal end in communication with the lumen 84, an opening 88 at the proximal end in communication with the lumen 84 (as shown in FIG. 9), and a handle 90 disposed at the proximal end of the tube 82 such that the handle 90 is disposed around the tube 82 and the opening 88, such that a flexible band or other implantable device can be inserted through the opening 88 at the proximal end of the cannula 80 and out of the tube 82 at the tip 86. As discussed above, the tip 86 is canted, resulting in a sharp tip 86. Alternatively, the tip 86 can have any known configuration so long as it can still perform the various functions described herein.

Figure 11:
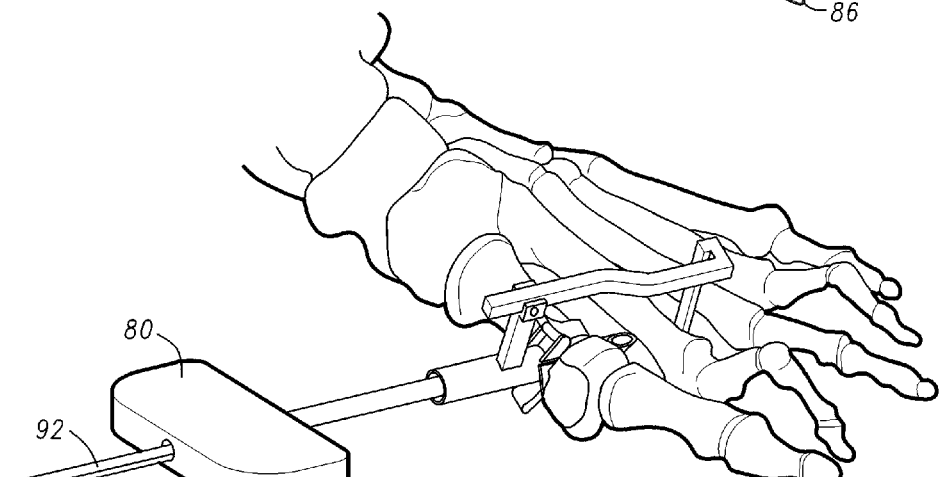
FIG. 11 is a perspective view of a leader component being inserted into an implantation cannula positioned in a drill guide positioned against a first metatarsal bone, according to one embodiment.
Figure 12:
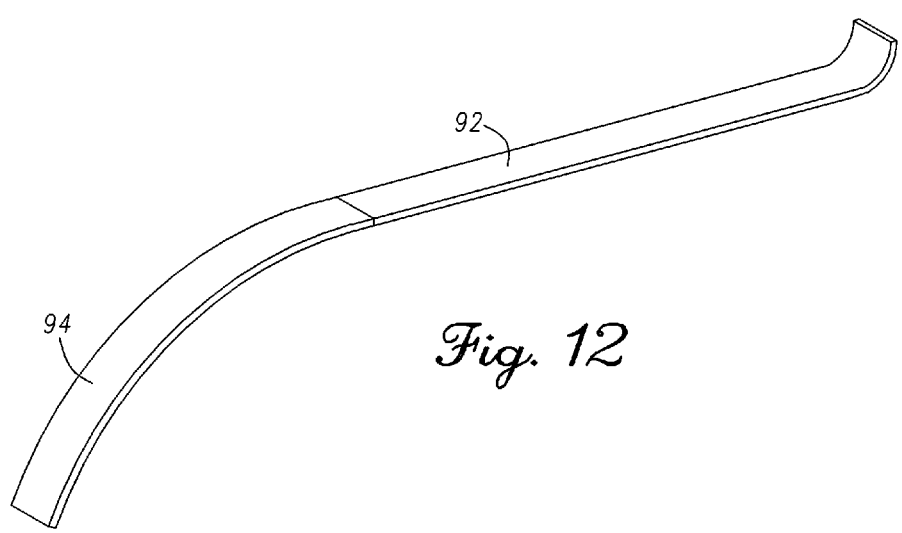
FIG. 12 is a perspective view of a leader component and flexible band, according to one embodiment.

In one implementation, once the cannula 80 is positioned as described above, the implantation of the flexible band can begin. As such, the first step for insertion of a flexible band is the insertion of a leader component 92 into and through the lumen 84 of the cannula 80 as shown in FIG. 11. More specifically, the leader component 92 is inserted into the opening 90 in the handle 88. As best shown in FIG. 12, the leader component 92 is coupled to the flexible band 94 for purposes of implantation of the flexible band 94. According to one embodiment, the leader component 92 is more rigid and less flexible than the flexible band 94 and makes insertion of the flexible band 94 through the devices described herein easier and thus facilitates implantation of the component 94.

As will be understood based on the procedures described herein, the leader component 92 can be made of any material that has sufficient rigidity or firmness to allow the leader component 92 to be urged through the cannula 80 and further be re-directed along the track 68 of the flexible band guide 60 while also having sufficient flexibility to allow for the re-direction or bending of the component 92 around the second metatarsal bone 34. In one embodiment, the leader component 92 is made up of a flexible, high tensile strength material. For example, the leader 92 in one embodiment is made of a solid polyester, which can optionally be configured in a ribbon configuration to impart greater flexibility in one dimension. Alternatively, the leader 92 can be made of stainless steel ribbon, polyamide, PTFE, or any other known flexible, high tensile strength material.

In contrast, the flexible band 94 is made of a substantially flexible material and is typically more flexible than the leader 92. In certain preferred versions, the flexible band 94 is comprised of a woven ribbon of polyester, such as Dacron. Alternatively the flexible band 94 can be fabricated from ultra high molecular weight polyethylene (UMWPE), PTFE, or any other known flexible hight tensile strength material. Configurations which optimize tensile strength and bending flexibility such as woven ribbon or stranded yarns are preferred. Alternatively, the flexible band 94 can elastic, and can be made of solid or woven silicone rubber, one of or a combination of two or more of silicone rubber, PEBA such as Pebax™, Kraton™ polymers, polyurethane, latex, or any other elastomeric materials that can be used in such implant devices as those describe herein. In another alternative, an elastic band is contemplated that is made of a commercially available knitted elastic material such as Lycra™ or Nylon™. In yet a further alternative embodiment, the flexible band is made of any known elastic material that could be used in a device as described herein. In other implementations, the flexible band 94 can be made of a bio-absorbable material such as poly-lactic acid, poly-L-lactic acid, or any known bioabsorbable material such as those used in biodegradable sutures.

In one implementation, the flexible band 94 is structured as a monofilament component. Alternatively, the flexible band 94 is a multifilament component. In a further embodiment, the flexible band 94 is a braided multifilament component.

In an alternative implementation in which the component 94 is a tension band 94, the tension band 94 is made of a "heat shrinkable" material such as, for example, a cross-linked polyolefin heat shrink in which the tension band 94 is coated or impregnated with an material such as metallic powder that can be heated inductively. Alternatively, the heat shrink material can be cross-linked PTFE. In a further embodiment, the heat shrink material can be any known material that can be shrunk, shortened, or otherwise reduced in size by the application of heat. In such an embodiment, the tension band 94 can initially be configured to have an untensioned (or original) length such that, when initially implanted with respect to the first and second metatarsal bones as described herein, the component 94 is configured to be untensioned. Once the tension band 94 is positioned correctly, heat can be applied to the tension band 94 such that the tension band 94 begins to shrink, thereby decreasing the untensioned length and resulting in a force being applied to the first metatarsal 32 urging it toward the second 34. Further heat can be applied over time to further shrink the tension band 94 and thus further decrease the untensioned length and result in further force being applied.

In one version, the heat energy that is applied to the heat shrink tension band 94 is RF energy. Alternatively, any known heat source capable of shrinking the heat shrink tension band 94 can be used. Further, it is understood that the heat can be applied regularly, such as daily, weekly, monthly, or at any other intervals. Alternatively, the heat can be applied as needed, such that the heat is only applied when the first metatarsal 32 has moved some predetermined distance toward the second metatarsal 34.

In further alternative embodiments, the tension component can be a spring, such as a tensioned spring or a heat-activated spring. Such springs can be made of a superelastic material, or a shape memory alloy (such as nitinol, for example). For example, the spring is made of any of stainless steel, titanium, tungsten, or a chromium cobalt alloy such as MP35N. In a further alternative, the spring is made of any known material that can be used in a tensioned spring or heat-activated spring for a device as described herein.

Figure 13:
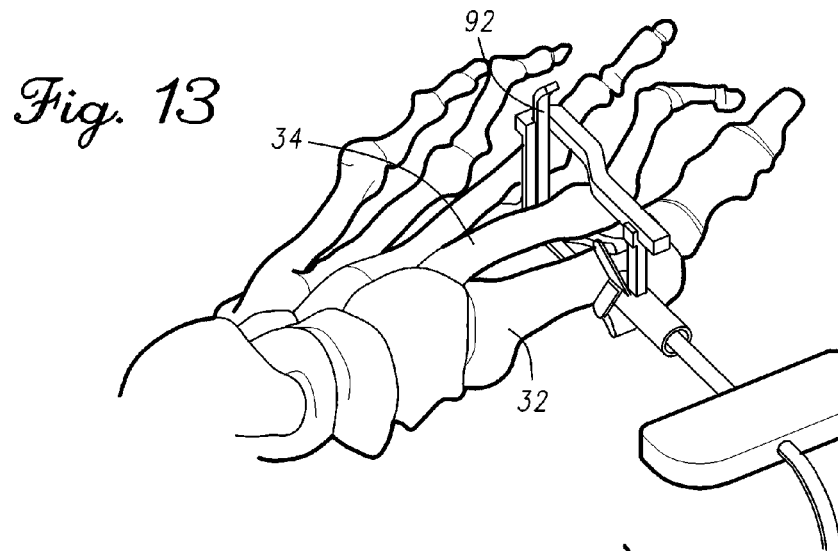
FIG. 13 is a perspective view of a leader component being inserted through an implantation cannula and urged upward along a track of a flexible band guide, according to one embodiment.

As shown in FIG. 13, the next step of the implantation procedure, according to one embodiment, is to urge the leader component 92 through the lumen 84 of the cannula 80 and against the receiving component 66 of the flexible band guide 60 (as best shown in FIG. 7). By doing so, the distal end of the leader component 92 is re-directed vertically along the track 68 of the second arm 64 and urged upward out of the incision between the second and third metatarsals 34, 36. This results in the leader component 92 to be positioned such that it is curved around the second metatarsal bone 34. According to one implementation, the guide 60 is then removed from the patient's foot. Subsequently, the tip 86 of the cannula 80 is positioned between the first and second metatarsals 32, 34. In an alternative implementation, the cannula 80, drill guide 30, and the flexible band guide 60 are all removed and then the cannula 80 is reinserted into the hole in the first metatarsal bone 32 and positioned between the first and second metatarsals 32, 34. Once the cannula tip 86 is in position, the distal end of the leader 92 is pulled over the top of the second metatarsal 34 toward the first metatarsal 32 by direct manipulation through the incision adjacent to the second metatarsal 34 and inserted into the opening 84 in the tip 86 of the cannula 80 and urged back through the lumen 84 and out the proximal end of cannula 80. According to one embodiment, the operator inserts the distal end of the leader 92 into the incision and back through the cannula 80 by hand. Alternatively, the distal end of the leader 92 can be inserted into the incision and back through the cannula 80 with a forceps or using any other known standard surgical tool or technique.

Figure 14:
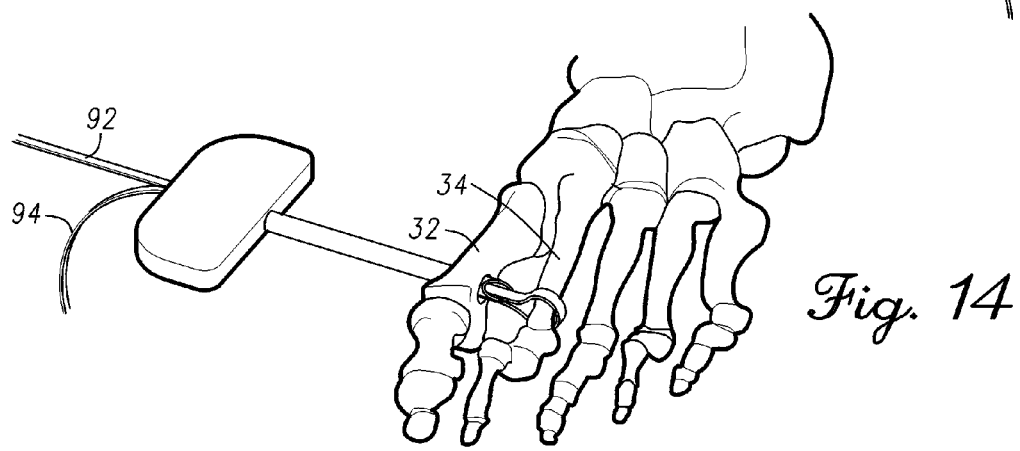
FIG. 14 is a perspective view of a leader component being pulled back out of the implantation cannula while the flexible band is being pulled into the hole in the first metatarsal bone, according to one embodiment.

Once the leader component 92 has been urged back through the hole in the first metatarsal bone 32 as shown in FIG. 14, in accordance with one embodiment the user pulls the leader component 92 in the direction away from the patient's foot such that the flexible band 94 coupled to the opposite end of the leader component 92 is pulled through the hole in the first metatarsal 32, around the second metatarsal 34, and back through the hole, thereby resulting in the band 94 being positioned through the hole and around the second metatarsal 34 as generally shown in FIG. 2 discussed above (except that the two ends of the band have not yet been coupled or fixed). At this point, the leader 92 may be removed from the flexible band 94.

Figure 15:
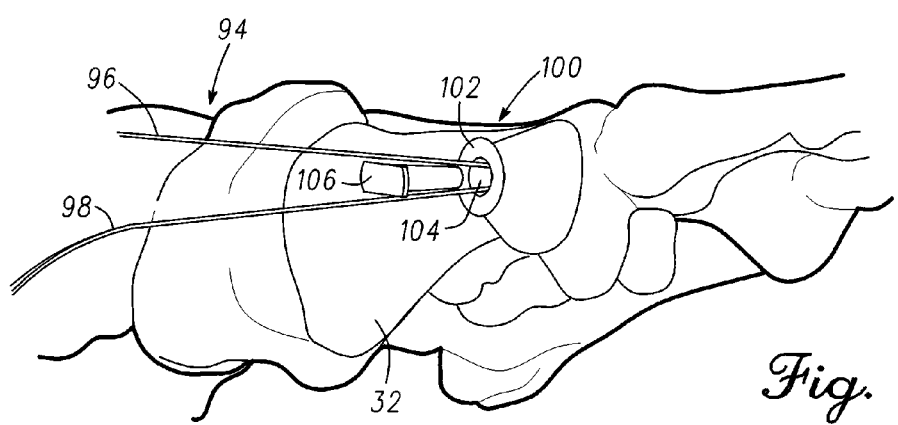
FIG. 15 is a perspective view of a locking mechanism positioned against a first metatarsal bone, according to one embodiment.
Figure 16A:
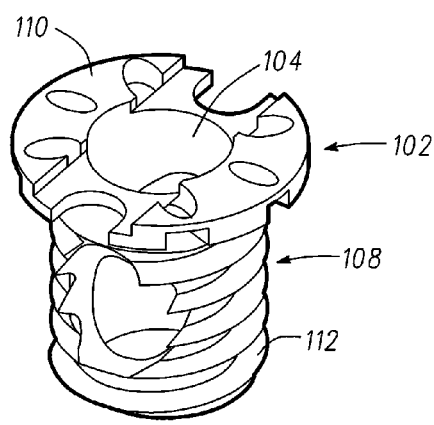
FIG. 16A is a perspective view of a base of a locking mechanism, according to one embodiment.
Figure 16B:
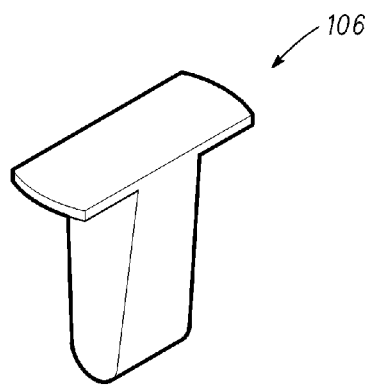
FIG. 16B is a perspective view of a wedge of a locking mechanism, according to one embodiment.

Once a flexible band has been correctly positioned according to any of the various implementations herein (or by any appropriate method of implantation) around a second metatarsal bone and through a hole in a first metatarsal bone (and the leader 92 has been removed), the two ends of the flexible band extending out of the hole in the first metatarsal are fastened together. In one embodiment as shown in FIG. 15, the two ends 96, 98 of the flexible band 94 are coupled to each other with a coupling component 100. In the embodiment as shown, the coupling component 100 is a locking mechanism 100 having a base 102 and a wedge 106. The base 102 is positioned against the first metatarsal bone 32 and defines an opening 104 that is adjacent to and in communication with the hole in the first metatarsal 32 such that the two ends 96, 98 extend through the opening 104. As shown in FIG. 16A, one embodiment of the base 102 has an anchor 108 and a flange 110. The anchor 108 is positioned inside the hole in the first metatarsal bone 32 such that the flange 110 is in contact with the outer surface of the bone 32 as best shown in FIG. 15. In this implementation, the anchor 108 has threads 112 that are configured to secure the base 102 in the hole of the bone 32. Alternatively, the anchor 108 is attached to the bone 32 by any known attachment method, material, or device. Alternatively, the base 102 is attached to the bone 32 via the frictional securement of the wedge as described below. The wedge 106, which is also depicted in FIG. 16B, is configured to be positioned in the opening 104 such that the wedge 106 is frictionally secured in contact with the two ends 96, 98 within the opening 104, whereby the two ends 96, 98 are frictionally secured between the wedge 106 and the base 102. Alternatively, the wedge 106 and base 102 can be configured such that they are secured to each other via a snap-fit mechanism, threads, or any other known type of coupling mechanism.

In a further embodiment, the coupling component 100 is a locking mechanism that includes the base 102 and a set of angled protrusions (not shown) positioned along the edges of the flexible band 94 that are configured to allow the ends 96, 98 of the component 94 to be pulled out through the base 102 but does not allow the component 94 to move in the opposite direction, thereby locking it in place. Alternatively, the coupling component 100 can be any device configured to fasten the two ends 96, 98 to each other, to the component 100, or to the first metatarsal bone 60. For example, in one alternative embodiment, the device can be an anchor such as one of the anchors disclosed in U.S. application Ser. No. 12/371,354, entitled "Methods and Devices for Treating Hallux Valgus" and filed on Feb. 13, 2009, which is incorporated herein by reference in its entirety.

Figure 17:
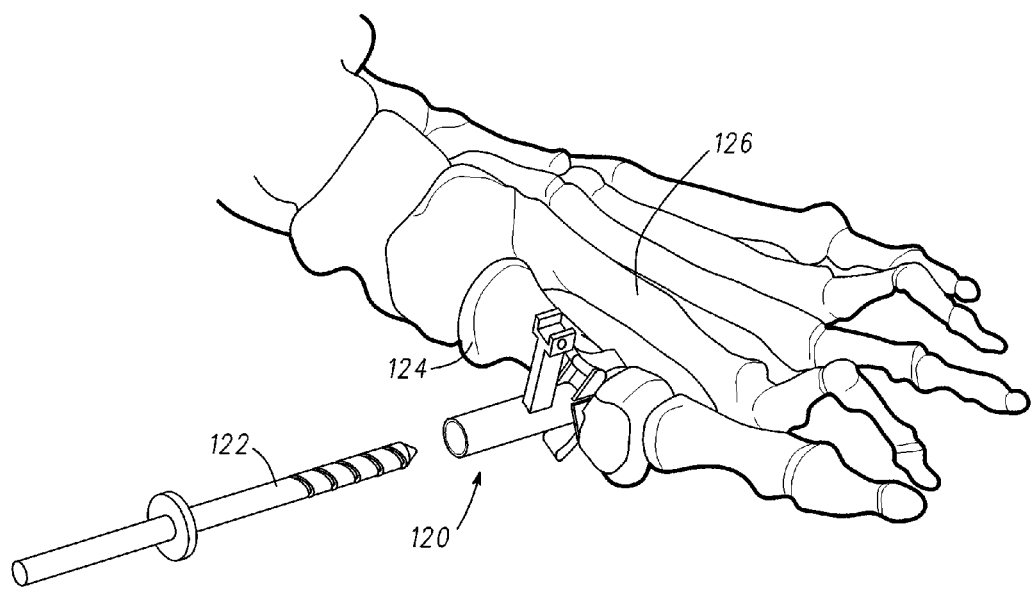
FIG. 17 is a perspective view of a drill being inserted into a drill guide positioned against a first metatarsal bone, according to an alternative embodiment.

FIGS. 17, 18, 19, and 20 depict an alternative implantation procedure, according to one embodiment. As shown in FIG. 17, in this embodiment a drill guide 120 is used without a flexible band guide. Thus, the drill guide 120 is positioned against the first metatarsal bone 124 and the drill 122 is then inserted into the drill guide 120 to drill a hole in the bone 124 in a fashion similar to that described above. As such, the skin incision adjacent the second metatarsal as described above can be avoided, and the entire implantation of the flexible band can be performed through a single incision on the medial aspect of the foot, adjacent the big toe.

Figure 18:
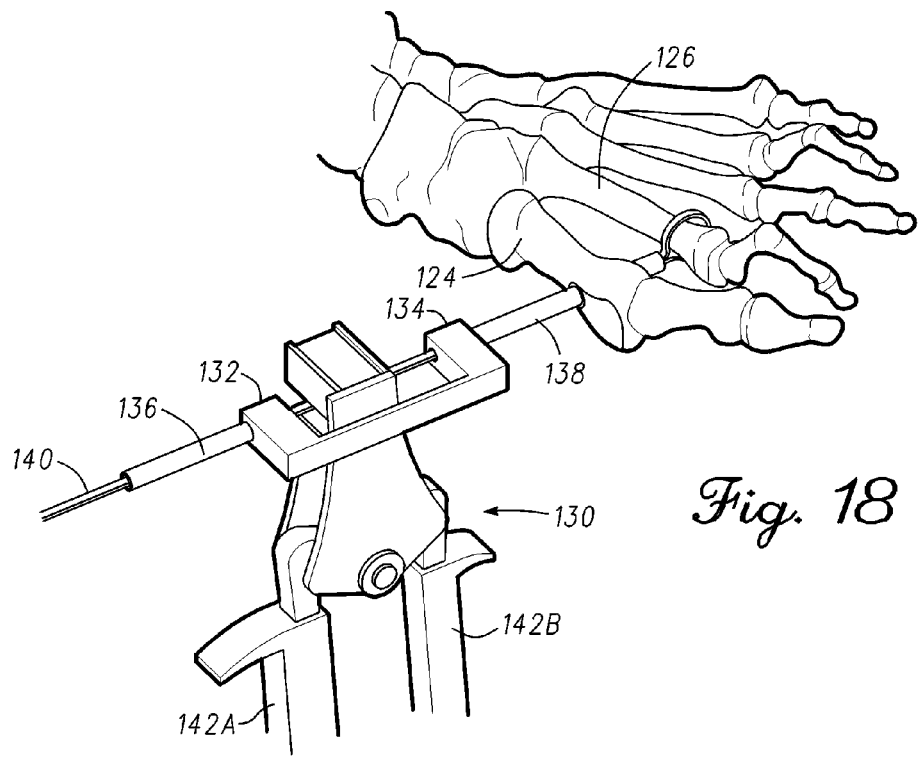
FIG. 18 is a perspective view of an insertion device being used to implant a flexible band into a foot, according to one embodiment.

As shown in FIG. 18, once the hole has been drilled using the drill guide 120, the drill guide 120 is removed and a flexible band delivery device 130 is used. The embodiment of the delivery device 130 shown from a rear perspective in FIG. 18 and a front perspective in FIG. 19 has a first arm 132 coupled to a first tube 136 and a second arm 134 coupled to a second tube 138. The first and second tubes 136, 138 are configured to receive a leader and flexible band 140 such that the leader and flexible band 140 is disposed within the first and second tubes 136, 138 and further is disposed in the space between the two tubes 136, 138 as best shown in FIG. 20. The delivery device 130 also has two pivotal handles 142A, 142B and a head portion 144. In addition, the delivery device 130 has a catch mechanism 150 that can be slidably positioned within the second tube 138. As described in further detail below, the catch mechanism 150 can be used to catch, retrieve, or otherwise assist with pulling the distal end of the leader and flexible band 140 back through the second tube 138 of the device after it has been properly positioned around the second metatarsal bone 126. It is understood that the leader and flexible band 140 can have a configuration similar to that described above with respect to other embodiments such that the component 140 has a leader portion and a flexible portion.

Figure 19:
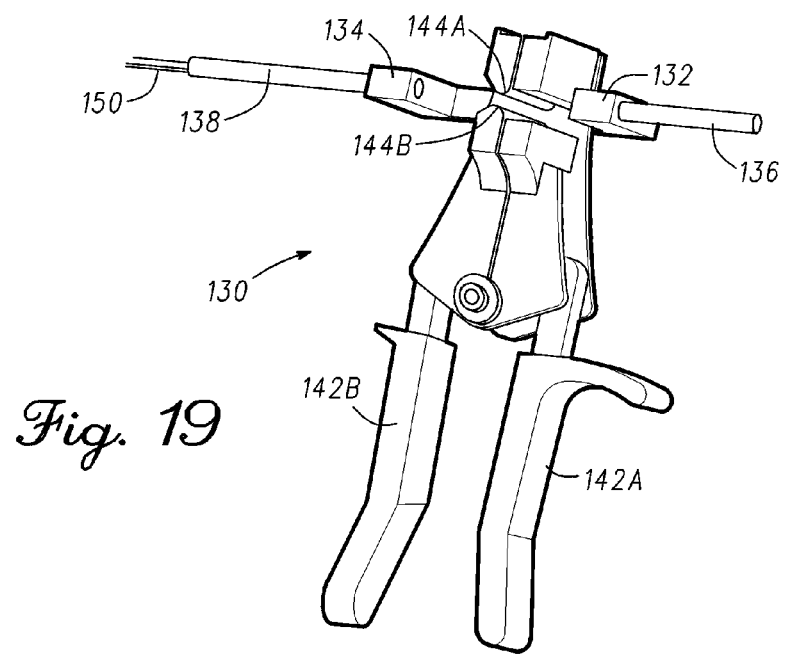
FIG. 19 is a perspective view of the insertion device of FIG. 18.
Figure 20:
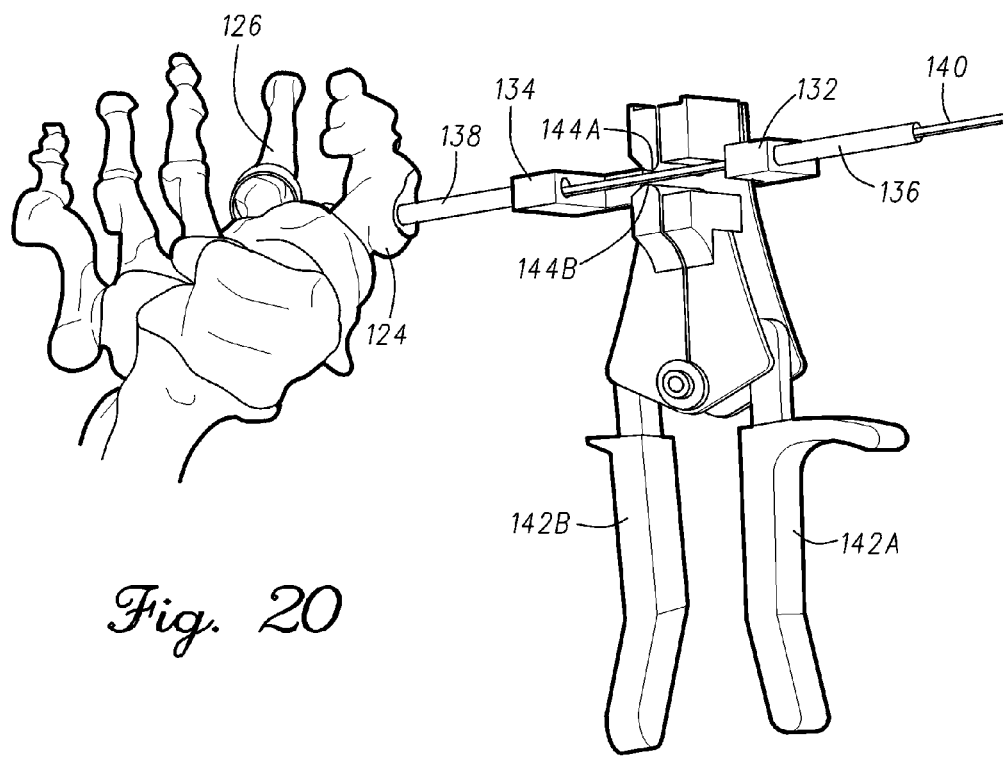
FIG. 20 is a different perspective view of the insertion device of FIG. 18.

According to one embodiment as best shown in FIGS. 19 and 20, the device 130 also has a drive mechanism 144 that is used to move the leader and flexible band 140 during implantation as explained in detail below. The drive mechanism 144 in this embodiment has first and second drive wheels 144A, 144B rotatably disposed adjacent to each other as shown such that the leader portion or flexible portion of the leader and flexible band 140 can be positioned between and in contact with both wheels 144A, 144B. The wheels 144A, 144B are coupled to the pivotal handles 142A, 142B such that moving the handles 142A, 142B causes the wheels 144A, 144B to rotate. In use, the leader and flexible band 140 can be frictionally urged in one direction or the other by rotating the wheels 144A, 144B. Alternatively, the drive mechanism 144 is, or is similar to, the drive mechanism found in a Strip-Easy™ Automatic Wire Stripper (Part # SE-92) available from Gardner Bender in Milwaukee, Wis. (not shown). Alternatively, the drive mechanism can be any known mechanism for urging forward a strand-like component such as a leader and flexible band.

In use, the delivery device 130 is configured to urge the leader and flexible band 140 through the hole in the first metatarsal bone 124, out of the second tube 138, under the second bone 126 and above the flexor tendon (not shown), and around the second metatarsal 126. First, the device 130 is positioned such that the second tube 138 is positioned into and through the hole in the first bone 124. Once the device 130 is positioned appropriately, the device 130 is used to insert the leader at the distal end of the flexible band 140 through the hole and around the second metatarsal bone 126. As described above, the device 130 is configured to urge the leader forward with the drive mechanism 144 that is disposed within or beneath the head portion 144 and is operably coupled to the pivotal handles 142A, 142B. Regardless of the exact configuration, the drive mechanism 144 is configured to urge the leader and flexible band 140 toward the patient's foot.

Figure 22:
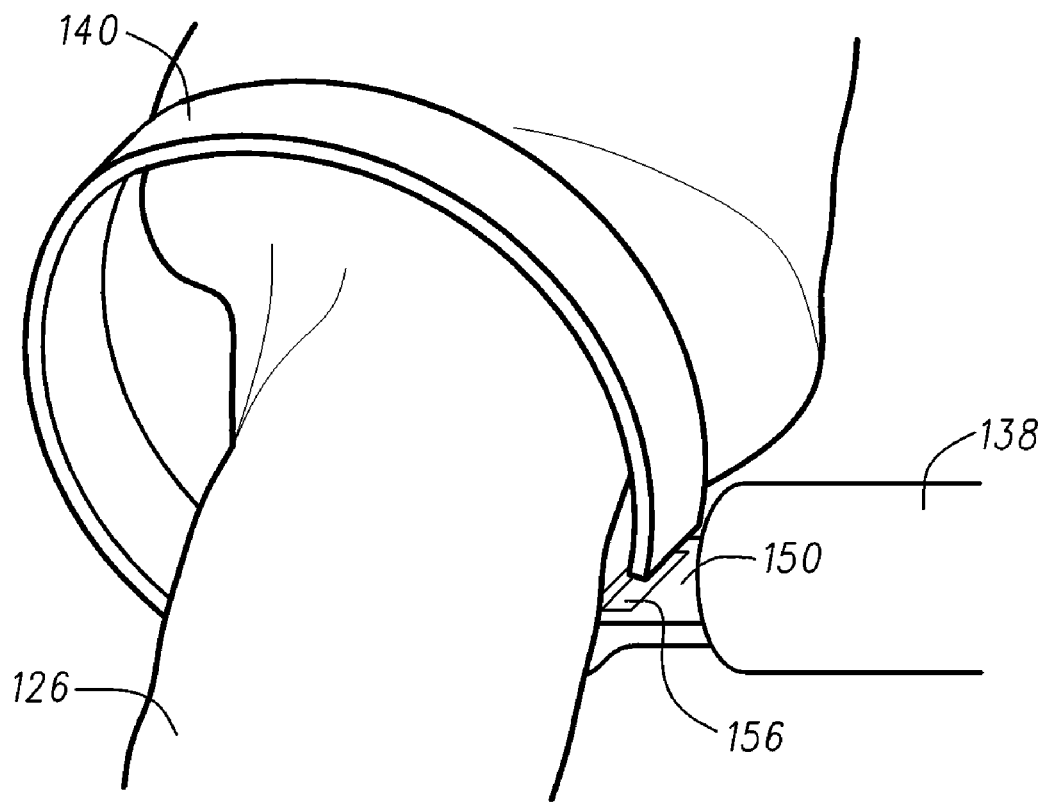
FIG. 22 is another perspective view of the catch mechanism of FIG. 21 in use, according to one embodiment.

In this embodiment, the leader portion of the flexible band 140 is configured to have a pre-formed curve at its distal end so that, as the leader 140 exits the second tube 138, the component 140 is urged through the tissue and automatically wraps around the second metatarsal bone 126 as best shown in FIG. 22. In one embodiment, the pre-formed curve is a precoiled ribbon that is in a tensioned state as it exits the second tube 138 such that the distal end moves upward as it is urged out of the tube 138, whereby the component 140 is urged upward between the second and third metatarsal bones 126, 128 and then across the top of the second metatarsal 126 back toward the first metatarsal 124, and then downward between the first and second metatarsals 124, 126 and ultimately in contact with the second tube 138.

Figure 21:
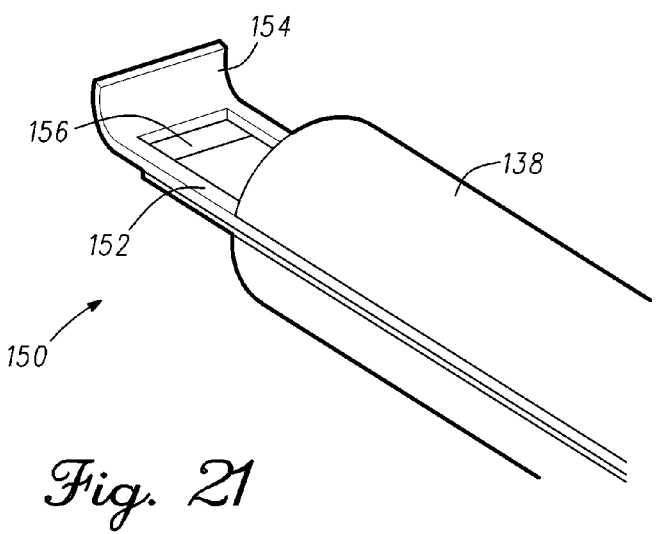
FIG. 21 is a perspective view of a catch mechanism, according to one embodiment.

According to one implementation as best shown in FIG. 21, the catch mechanism 150 disposed within and out of the end of the second tube 138 can be coupled to the end of the leader portion of the component 140 after the leader has been positioned around the first metatarsal bone 124 to pull the distal end of the component 140 back into and through the second tube 138. The catch mechanism 150 as shown is an elongate component having an elongate body 152 and a hole 156 defined near the distal end of the mechanism 150. In the depicted embodiment, the catch mechanism 150 has a curved end 154 to assist with engagement with the distal end of the leader. Alternatively, the catch mechanism 150 has no curved end. The catch mechanism 150 is slidable within or along the second tube 138 such that the curved end 154 and hole 154 can be positioned out of the end of the second tube 138. Alternatively, the catch mechanism 150 can be any known mechanism or device that can be used to engage or couple with the leader as described below.

In use, in accordance with one embodiment, when the distal end of the component 140 wraps around the bone 126 as best shown in FIG. 22, it couples with the catch mechanism 150 positioned through and out of the tube 138. More specifically, the distal end of the component 140 is inserted into and/or through the hole 156 in the catch mechanism 150, thereby coupling the component 140 to the mechanism 150. The catch mechanism 150 can then be pulled back through the tube 138, thereby pulling the distal end of the leader and flexible band 140 through the tube 138 as well. Alternatively, the entire delivery device 130 can be moved away from the patient's foot such that the second tube 138 is removed from the hole in the first bone 124 such that the distal end of the component 140 is also urged through the hole.

Once the component 140 has been pulled out through the hole, the component 140 is positioned such that it is wrapped around the second metatarsal bone 126 and through the hole in the first metatarsal bone 124 in a fashion similar to that described with respect to the prior embodiments discussed above. Thus, the leader is removed and the two ends of the flexible band 140 extending out of the hole can be secured or fixed in any fashion described above.

Although the present invention has been described with reference to preferred embodiments, persons skilled in the art will recognize that changes may be made in form and detail without departing from the spirit and scope of the invention.

What is claimed is:

1. A method of treating a bone deformity comprising:
   positioning a drill guide against a first bone;
   coupling a tension band guide having a receiving track to the drill guide;

drilling a hole through the first bone;
inserting an implantation cannula through the drill guide and the hole in the first bone;
inserting a tension band through the implantation cannula and into contact with the tension band guide such that the tension band is urged through the hole in the first bone, around a second bone via the tension band guide, and back through the hole in the first bone; and
locking the tension band in place with a locking mechanism wherein the step of inserting a tension band includes
inserting a first end of a leader component through the implantation cannula and into contact with the receiving track, wherein a second end of the leader component is coupled to the tension band;
urging the first end of the leader component against the receiving track such that the first end of the leader component is redirected by the receiving track upward on the side of the second bone that is opposite the first bone;
urging the first end of the leader component over the second bone in a direction toward the first bone and through the hole in the first bone;
pulling the first end of the leader component through the hole in the first bone such that the tension band is urged through the hole in the first bone, around the second bone, and back through the hole in the first bone; and
detaching the leader component from the tension band.

2. The method of claim 1, wherein the first bone is a first metatarsal bone and the second bone is a second metatarsal bone.

3. The method of claim 2, further comprising locking the tension band such that the tension band is under tension, whereby the tension band causes a reduction in an intermetatarsal angle.

4. The method of claim 1, wherein coupling the tension band guide to the drill guide further comprises positioning a receiving track adjacent to a second bone and on a side of the second bone that is opposite the first bone.

5. The method of claim 1, wherein inserting the implantation cannula further comprises positioning the implantation cannula into contact with an underside of the second bone.

6. The method of claim 1, wherein the tension band is elastic.

7. The method of claim 1, wherein the tension band is a flexible band.

* * * * *